United States Patent

Baxter et al.

[11] Patent Number: 4,686,217
[45] Date of Patent: Aug. 11, 1987

[54] CALCIUM ANTAGONIST 2-FLUOROALKYL-1,4-DIHYDROPYRIDINES

[75] Inventors: Andrew J. G. Baxter, Keyworth; John Dixon, Belton; Kenneth J. Gould, Long Whatton; Alan C. Tinker, Loughborough, all of England

[73] Assignee: Fisons plc, Ipswich, England

[21] Appl. No.: 601,309

[22] Filed: Apr. 17, 1984

[30] Foreign Application Priority Data

Apr. 27, 1983 [GB] United Kingdom ............ 8311519
Oct. 1, 1983 [GB] United Kingdom ............ 8326362
Nov. 18, 1983 [GB] United Kingdom ............ 8330852
Dec. 22, 1983 [GB] United Kingdom ............ 8334285

[51] Int. Cl.⁴ ............ A61K 31/455; C07D 211/90; C07D 401/04; C07D 413/04
[52] U.S. Cl. ............ 514/210; 514/318; 514/333; 514/334; 514/336; 514/338; 514/356; 546/193; 546/194; 546/256; 546/258; 546/268; 546/271; 546/275; 546/321
[58] Field of Search ............ 546/321, 256, 268, 258, 546/275, 271, 193, 194; 424/266; 514/356, 333, 334, 338, 210, 318, 336

[56] References Cited

U.S. PATENT DOCUMENTS 4,031,104 6/1977 Bossert et al. ............ 546/321
4,307,103 12/1981 Sato et al. ............ 546/321

FOREIGN PATENT DOCUMENTS 0063359 10/1982 European Pat. Off. .
0080220 6/1983 European Pat. Off. .
2629892 1/1977 Fed. Rep. of Germany .

OTHER PUBLICATIONS

Singh, B. et al, Chem. Abstacts, 94:15508m.
Balicki, R. et al, Chem. Abstracts 82:72,739p.

Bossert et al, "4-Aryldihydropyridines", Angew. Chem. Int. Ed. Engl., 20 (1981), pp. 762–769.
Schramm et al, "Novel Dihydropyridines with Positive Inotropic Action", Nature, vol. 303 (9 Jun. 1983), pp. 535–537.

Primary Examiner—Henry A. Jiles
Assistant Examiner—Dale A. Bjorkman
Attorney, Agent, or Firm—Marshall, O'Toole, Gerstein, Murray & Bicknell

[57] ABSTRACT

There are described compounds of formula I,

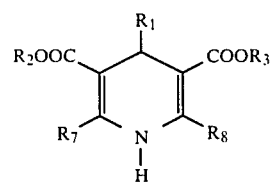

in which
$R_1$ represents benzofurazanyl, pyridyl or phenyl, the pyridyl or phenyl being substituted,
—$COOR_2$ and —$COOR_3$ are various ester groups,
one of $R_7$ and $R_8$ represents alkyl C1 to 6 and the other represents —$CONR_{10}R_{11}$; —$CSNH_2$; —$C(=NH)SR_9$; —$S(O)_mR_9$; phenyl optionally substituted by one or more of alkyl C1 to 6, halogen, alkoxy C1 to 6 or nitro; alkyl C1 to 6 substituted by halogen; or furanyl;
m is 0 or 1
$R_9$ is alkyl C1 to 6, and
$R_{10}$ and $R_{11}$ each independently represent hydrogen or alkyl C1 to 6, or together with the nitrogen atom to which they are attached form a 5 or 6 membered heterocyclic ring.

There are also described processes for making the compounds, and pharmaceutical, e.g. calcium antagonist, formulations containing them.

10 Claims, No Drawings

CALCIUM ANTAGONIST 2-FLUOROALKYL-1,4-DIHYDROPYRIDINES

This invention relates to new compounds, methods for their preparation and compositions containing them.

A wide variety of dihydropyridines have been described as being useful as pharmaceuticals and some, notably nifedipine, have been sold for this use.

We have now found a new group of pyridine derivatives which have pharmacological activity.

According to the invention we provide compounds of formula I,

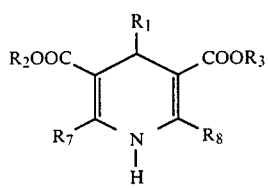

in which
- $R_1$ represents benzofurazanyl, pyridyl or phenyl, the pyridyl or phenyl being substituted by one or more of the groups halogen, nitro, —CN, —$OR_9$, —S(O)$_p R_9$, or alkyl C1 to 6 optionally substituted by halogen,
- p is 0, 1 or 2,
- $R_2$ and $R_3$, which may be the same or different, each represent hydrogen; alkyl C1 to 6 optionally substituted by one or more of the groups halogen, cyano, —$XR_4$, —$NR_5R_6$ or phenyl; cycloalkyl C3 to 8 optionally substituted by alkyl C1 to 6; a 4, 5 or 6 membered oxygen or nitrogen containing heterocyclic ring which is optionally substituted by alkyl C1 to 6 the alkyl in turn optionally being substituted by one or more phenyl groups;
- $R_5$ and $R_6$ which may be the same or different, each represent alkyl C1 to 6 optionally substituted by phenyl,
- one of $R_7$ and $R_8$ represents alkyl C1 to 6 and the other represents —$CONR_{10}R_{11}$; —$CSNH_2$; —C(=NH)$SR_9$; —S(O)$_m R_9$; phenyl substituted by one or more of alkyl C1 to 6, halogen, alkoxy C1 to 6 or nitro; alkyl C1 to 6 substituted by halogen; or furanyl,
- X is O or S,
- m is 0 or 1,
- $R_4$ is alkyl C1 to 6 or phenyl,
- $R_9$ is alkyl C1 to 6,
- $R_{10}$ and $R_{11}$ each independently represent hydrogen or alkyl C1 to 6, or together with the nitrogen atom to which they are attached form a 5 or 6 membered heterocyclic ring, provided that when
(i) $R_1$ represents benzofurazanyl then $R_8$ does not represent —$CF_3$, or
(ii) $R_1$ represents 2-nitrophenyl, or 2-chlorophenyl and $R_2$ and $R_3$ are both ethyl, then $R_8$ does not represent mono-chloromethyl, and pharmaceutically acceptable acid addition salts of those compounds containing a basic nitrogen atom.

According to the invention we also provide the compounds of formula I without proviso (ii) for use as pharmaceuticals.

According to the invention we further provide a process for the production of a compound of formula I, or a pharmaceutically acceptable acid addition salt thereof, which comprises (a) reaction of a compound of formula II, $$R_1 CHO \qquad \qquad II$$

with compounds of formulae III and IV, $$R_2OOCCH=C(R_7)NH_2 \qquad \qquad III$$

$$R_3OOCCH_2COR_8 \qquad \qquad IV$$

in which formulae $R_1$, $R_2$, $R_3$, $R_7$ and $R_8$ are as defined above, (b) reaction of a compound of formula V, $$R_1CH=C(COOR_3)COR_8 \qquad \qquad V$$

in which $R_1$, $R_3$ and $R_8$ are as defined above, with a compound of formula III, (c) production of a compound of formula I by dehydration of a compound of formula VII,

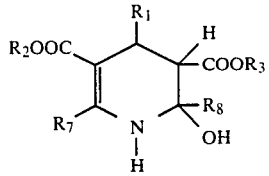

in which $R_1$, $R_2$, $R_3$, $R_7$ and $R_8$ are as defined above, (d) production of a compound of formula I in which m is 1 or p is 1 or 2 by selective oxidation of a corresponding compound of formula I in which m is 0, or p is 0 or 1 respectively, (e) production of a compound of formula I in which one of $R_7$ and $R_8$ is —$CONR_{10}R_{11}$ by reaction of an acid halide, imidazole or a mixed anhydride of a corresponding compound of formula I in which one of $R_7$ and $R_8$ is —COOH with a compound $HNR_{10}R_{11}$ in which $R_{10}$ and $R_{11}$ are as defined above, or, when the group —$NR_{10}R_{11}$ in the product represents an imidazole, reacting the free carboxylic acid of formula I with N,N'-carbonyldiimidazole, (f) production of a compound of formula I in which one of $R_7$ and $R_8$ is —$CSNH_2$ by reaction of a corresponding compound of formula I in which one of $R_7$ and $R_8$ is —CN with hydrogen sulphide, (g) isomerising a 3,4-dihydropyridine to a corresponding compound of formula I, (h) production of a compound of formula I in which one of $R_7$ and $R_8$ is —C(=NH)$SR_9$ by reaction of a corresponding compound of formula I in which one of $R_7$ and $R_8$ is —$CSNH_2$ with a compound $R_9$-hal, in which $R_9$ is as defined above and hal is a halogen atom, (i) reaction of a compound of formula IV with ammonia and a compound of formula VI, $$R_1CH=C(COOR_2)COR_7 \qquad \qquad VI$$

or reaction of a compound of formula V with ammonia and a compound of formula VIII, $$R_2OOCCH_2COR_7 \qquad \qquad VIII$$

or reaction of compounds of formulae II, IV and VIII with ammonia, in which formulae $R_1$, $R_2$, $R_3$, $R_7$ and $R_8$ are as defined above, (j) production of a compound of formula I in which one of $R_7$ and $R_8$ is —$CHF_2$ or —$CH_2F$ by reaction of a corresponding compound of formula I in which one of $R_7$ and $R_8$ is —CHO or —$CH_2L$, where L is —OH or a good leaving group, respectively with a fluorinating agent, (k) production of a compound of formula I in which at least one of $R_2$ and $R_3$ is hydrogen by reductive cleavage or hydrolysis of a corresponding compound of formula I in which at least one of $R_2$ and $R_3$ is other than hydrogen, (l) production of a compound of formula I in which at least one of $R_2$ and $R_3$ is other than hydrogen by esterification or transesterification of a corresponding compound of formula I in which at least one of $R_2$ and $R_3$ is hydrogen or is a group $R_2$ or $R_3$ other than that desired in the end product, or (m) production of an optical isomer of a compound of formula I by resolution of a mixture of optical isomers of the compound, and where desired or necessary converting the resulting compound of formula I to a pharmaceutically acceptable acid addition salt thereof or vice versa.

The reaction of process (a) may be carried out by subjecting the compounds of formulae II, III and IV to an elevated temperature, e.g. of from about 20° to 140° C. in the presence or absence of a suitable solvent, e.g. a lower alkanol.

Processes (b) and (i) may be carried out under similar conditions to process (a). In processes (a), (b) and (i) dehydration is generally required as a separate process step when $R_8$ is an electron withdrawing group, e.g. —$CF_3$, perhaloalkyl-, nitro- or mono- or di-chlorophenyl or unsubstituted phenyl. The presence of a base, e.g. diethylamine or ammonia, tends to inhibit dehydration in these processes. We prefer not to use process (a), (b) or (i) when $R_7$ or $R_8$ is —C(=NH)$SR_9$ or when $R_2$ or $R_3$ is hydrogen.

Process (c) may be carried out in a solvent which is inert under the reaction conditions, e.g. methylene chloride, and in the presence of a dehydrating agent, e.g. trifluoroacetic anhydride, and a base, e.g. pyridine. The dehydration may also be effected using diethylaminosulphur trifluoride. The reaction may be carried out at from about 0° to 40° C. The compounds of formula VII may be formed as intermediates, which may or may not be isolated, in processes (a), (b) and (i). Under certain circumstances, e.g. when $R_8$ is not an electron withdrawing group, the compound of formula VII may dehydrate spontaneously to yield the compound of formula I. When diethylaminosulphur trifluoride is used in this process and $R_8$ is $CH_2OH$ or CHO in the starting material the —$CH_2OH$ or —CHO will, as in process (j), be converted to —$CH_2F$ and —$CHF_2$ respectively.

Process (d) may be carried out using a suitable oxidising agent, e.g. peracetic acid. The reaction may be carried out in a suitable solvent, e.g. a mixture of methanol and acetic acid. We prefer not to use this process when $R_7$ or $R_8$ is —C(=NH)$SR_9$.

Process (e) may be carried out by treating the acid halide, imidazole or the mixed anhydride (which compounds may be prepared by conventional processes known per se), with aqueous ammonia or the amine $HNR_{10}R_{11}$ at a temperature of from 0° to 30° C. We prefer not to use this process when $R_2$ or $R_3$ is hydrogen.

Process (f) may be carried out by treating the nitrile starting material with hydrogen sulphide gas in a suitable solvent, e.g. pyridine. The reaction is preferably carried out in the presence of a base, e.g. triethylamine, and may conveniently be carried out at a temperature of from 10° to 30° C.

Process (g) may be carried out under basic conditions, e.g. in the presence of an alkylamine such as triethylamine. This process is particularly applicable when $R_8$ is both electron withdrawing and bulky.

Process (h) may be carried out in a solvent which is inert under the reaction conditions, e.g. diethyl ether. We prefer hal to be iodine.

Process (j) is preferably carried out at a temperature of from about —70° to 100° C., and in a solvent which is inert under the reaction conditions, e.g. a halogenated hydrocarbon and preferably methylene chloride. The fluorinating agent is preferably a dialkylaminosulphur trifluoride, e.g. diethylaminosulphur trifluoride, or (2-chloro-1,1,2-trifluoroethyl)diethylamine. The group L may be, for example, —$OSO_2Rx$, where Rx is alkyl C1 to 6, e.g. methyl, or aryl, e.g. p-tolyl.

The reductive cleavage of process (k) may be carried out chemically, e.g. using zinc and formic acid. The reaction may conveniently be carried out in a solvent which is inert under the reaction conditions, e.g. acetonitrile. When process (k) involves a hydrolysis the hydrolysis may be carried out using conventional techniques known per se.

Process (l) may, when it involves an esterfication, be carried out using the appropriate alcohol, preferably in excess and in the presence of a dehydrating agent, e.g. dicyclohexylcarbodiimide, or under similar conditions to process (e). The reaction may conveniently be carried out in a solvent which is inert under the reaction conditions, e.g. ethyl acetate. When a transesterification is involved the process may be carried out by treating the starting ester with the sodium alcoholate corresponding to the desired ester moiety.

The resolution of process (m) may be carried out by means of conversion of the mixture to, when $R_2$ or $R_3$ is H, a salt with an optically active base or an ester with an optically active alcohol (e.g. $CCl_3(C_6H_5)CHOH$ or $C_6H_5(OCH_3)CHCH_2OH$), or, when $R_2$ or $R_3$ is aminoalkyl, a salt with an optically active acid and separation of the product by selective crystallisation, or, preferably, by means of high performance liquid chromatography (HPLC). The separated product may then be converted to the desired optically active acid or ester by, for example, process (k) or (l).

The starting materials for the above processes are either known, or if they are not specifically known they may be made by processes described in the Examples, or they may be made from known compounds using one or more process steps which are known per se or are analogous to those described in the Examples.

Certain of the compounds of formula II are novel and the invention therefore also provides those compounds of formula II in which $R_1$ is 2-chloro-3-trifluoromethyl phenyl or phenyl substituted by three substituents selected from chloro-, fluoro- and —$CF_3$. Specifically we provide 2,3-dichloro-6-fluorobenzaldehyde, 3-chloro-6-fluoro-2-(trifluoromethyl)benzaldehyde and 2-chloro-3-(trifluoromethyl)benzaldehyde.

The compounds of formula I and the intermediates therefor may be isolated from their reaction mixtures using conventional processes, e.g. crystallisation or chromatography.

The compounds of formula I, and the pharmaceutically acceptable salts thereof, are useful because they exhibit pharmacological properties in animals. More particularly they block the entry of calcium into vascular and cardiac muscle leading to falls in blood pressure, inotropy and heart rate. They are active in the following systems:

(a) Relaxation of contracted vascular smooth muscle. Van Breemen, Aaronson, Loutzenhiser and Meisheri, Chest, 78, Supplement, 157–165, 1980.

(b) Reduction of inotropy and chronotropy of isolated atria. Henry, Excerpta Med. Int. Congr. Ser., 474, 14–23, 1979.

(c) Reduction of blood pressure and increase cardiac output in anaesthetised dogs. Hirakawa, Ito, Kondo, Watanbe, Hiei, Banno & Hyase, Arzneim-Forsch, 22, 344–349, 1972.

(d) Reduction of blood pressure in conscious dogs when given by the intravenous and oral routes. Newman, Bishop, Peterson, Leroux & Horowitz, J Pharm. Exp. Ther. 201, 723–730, 1977.

The compounds are thus indicated for use in the treatment of renovascular, malignant or essential hypertension (including hypertensive emergencies), pulmonary hypertension, vasospastic angina, chronic stable angina and congestive heart failure. Other indications are the treatment of renal failure, cardiac arrhythmias, hypertrophic cardiomyopathy, cerebrovascular diseases (including cerebral haemorrhage, ischaemia and vasospasm, migraine, altitude sickness and hearing loss), peripheral vascular diseases (including Raynauds syndrome, intermittent claudication and digital ulceration); use as a cardioplegic agent during surgery e.g. in cardiopulmonary bypass, and for the treatment of, and protection against, myocardial infarction and ischaemia.

By virtue of their ability to inhibit calcium entry into other cells and tissues the compounds are also indicated in the treatment of thrombosis, atherosclerosis, respiratory diseases (including asthma and bronchitis) glaucoma, aldosteronism, uterine hypermotility and for the relief of oesophageal and skeletal muscle spasm.

For the above uses the dosage will depend upon the compound used, the route of administration and the effect desired, but in general will be in the range of 0.1–10 mg per kilogram body weight per day. For man the indicated total daily dose will be from about 5–500 mg, preferably from 5 to 200 mg and more preferably from 5 to 100 mg, which may be administered preferably once daily, or in divided doses of about 1–200 mg, preferably 2 to 25 mg, e.g. 2 to 4 times per day.

The compounds of formula I are advantageous in that they possess greater potency (e.g. with respect to hypotensive and direct negative chronotropic effects), produce a lower level of reflex tachycardia, are more selective (e.g. for vascular smooth muscle vs cardiac muscle), produce less depression of cardiac contractility, are longer acting, are more readily absorbed or less readily metabolised, are more easily formulated, possess less, or less undesirable, side effects, are more stable or have other more beneficial properties than known compounds of similar structure.

The compounds of the invention may be administered by a wide variety of routes and may act systemically or locally. Thus the compounds may be administered by oral or nasal inhalation to the lung, to the buccal cavity, oesophageally, rectally, topically to the skin, the eye or to other available surfaces of the body; by injection, e.g. intravenously, intramuscularly, intraperitoneally, or by surgical implant.

When $R_2$ and/or $R_3$ represents a 4, 5 or 6 membered oxygen or nitrogen containing heterocyclic ring that ring may be an oxetanyl, azetidinyl, piperidinyl or tetrahydropyranyl ring. $R_2$ and/or $R_3$ may also represent —$(CH_2)_nXR_4$, —$(CH_2)_nCN$, —$CH(C_6H_5)$ $CCl_3$ or —$(CH_2)_nR_5R_6$ in which n is 4, 3 or preferably 2.

When $R_{10}$ and $R_{11}$ together with the nitrogen atom to which they are attached form a 5 or 6 membered heterocyclic ring we prefer that ring to be a morpholino or imidazolyl ring.

We prefer compounds of formula I in which one of $R_7$ and $R_8$ is methyl. We further prefer those compounds in which one of $R_7$ and $R_8$ is mono-, di- or trifluoromethyl. We particularly prefer one of $R_7$ and $R_8$ to be mono-fluoromethyl.

Groups $R_8$ which are electron withdrawing include alkyl C1 to 6 substituted by 2 or more halogen atoms; furanyl and phenyl substituted by one or more of alkyl C1 to 6, halogen, alkoxy C1 to 6 or nitro. Preferred electron withdrawing significances of $R_8$ are —$CCl_3$, —$CF_3$, —$CF_2 CF_3$, 4-nitrophenyl, 3,4-dichlorophenyl, 4-chlorophenyl and 3-chlorophenyl.

Values for $R_1$ include nitrophenyl; (trifluoromethyl)-phenyl; mono- or poly-fluorophenyl; mono- or poly-chlorophenyl; chloro- and/or fluoro-(trifluoromethyl)-phenyl; (alkylthio)pyridyl; alkyl- and/or chloro- and/or alkoxy-nitrophenyl; mixed chloro- and fluoro-phenyl; mono- or poly-alkoxy-phenyl; alkylphenyl; (alkylthio)-phenyl; (alkylsulphonyl)phenyl; and 4-benzofurazanyl. Values for $R_2$ and $R_3$ are alkyl C1 to 4, 2-alkoxy C1 to 3 - ethyl, 2-phenoxy-ethyl, cycloalkyl C4 to 6 optionally substituted by methyl, the saturated 4, 5 or 6 membered heterocyclic groups as defined immediately above and optionally substituted by phenylmethyl or diphenylmethyl, alkyl C1 to 4 -(phenylmethyl)aminoethyl, cyano- or alkyl C1 to 4 -thioalkyl C1 to 4; phenyl alkyl C1 to 4 or —$CH(C_6H_5)CCl_3$. Values of $R_8$ are chloro- or fluoro- alkyl C1 or 2, —$CSNH_2$, —$CON(alkyl\ C\ 1\ to\ 4)_2$, —$COmorpholino$, —$COimidazolyl$, —$C(=NH)S$-alkyl C1 to 4, —$S$-alkyl C1 to 4, —$S(O)$-alkyl C1 to 4, or phenyl substituted by one or two chlorine, nitro, methoxy or methyl groups, e.g. in the 4- and/or 3- positions. $R_7$ may be methyl. The Examples illustrate various permutations of substituents. The individual substituents exemplified may also be permutated in other combinations.

As a preferred group of compounds of formula I we provide those in which $R_1$ is phenyl carrying a 2-nitro or a 2—$CF_3$ group or at least two substituents selected from chloro; fluoro; alkyl C1 to 6, e.g. methyl; —$CF_3$ and nitro; $R_2$ is alkyl C1 to 6, e.g. isopropyl, cyclopentyl or cyclobutyl or is oxetan-3-yl; $R_3$ is alkyl C1 to 6, e.g. methyl; $R_7$ is alkyl C1 to 6, e.g. methyl; and $R_8$ is fluoromethyl, e.g. mono-, di- or tri-fluoromethyl.

As a most preferred group of compounds of formula I we provide those in which $R_1$ is phenyl carrying at least two substituents selected from chloro, fluoro, —$CF_3$, methyl and nitro, $R_3$ and $R_7$ are both methyl, $R_8$ is —$CH_2F$ and $R_2$ is isopropyl or cyclopentyl.

A specific group of compounds of formula I are those in which $R_1$ represents benzofurazanyl, pyridyl or phenyl, the pyridyl or phenyl being substituted by one or more of the groups halogen, nitro, trihalomethyl or —$SR_9$; $R_2$ and $R_3$ each represent alkyl C1 to 6, —$(CH_2)_nR_4$, —$(CH_2)_nCN$, —$CH(C_6H_5)CCl_3$ or —$(CH_2)_n NR_5R_6$; one of $R_7$ and $R_8$ represents alkyl C1 to 6 and the other represents —$CONR_{10}R_{11}$; —$CSNH_2$; —$C(=NH)SR_9$; —$S(O)_mR_9$; phenyl substituted by one or more of alkyl C1 to 6, halogen, alkoxy C1 to 6 or nitro; or alkyl C1 to 6 substituted by halogen; $R_4$ and $R_9$ are each alkyl C1 to 6; and $R_{10}$ and $R_{11}$ each represent hydrogen or alkyl C1 to 6, and provisos (i) and (ii) apply.

According to our invention we also provide a pharmaceutical composition comprising preferably less than 80%, more preferably less than 50%, e.g. 1 to 20%, by weight of a compound of formula I, or a pharmaceutically acceptable salt thereof, in admixture with a pharmaceutically acceptable adjuvant, diluent or carrier.

Thus the compound may be put up as a tablet, capsule, dragee, suppository, suspension, solution, injection, implant, a topical, e.g. transdermal, preparation such as a gel, cream, ointment, aerosol or a polymer system, or an inhalation form, e.g. an aerosol or a powder formulation.

We prefer compositions which are designed to be taken oesophageally and to release their contents in the gastrointestinal tract. Thus we prefer tablets which may, for example, be made by direct compression. In such a process the active ingredient is mixed with one or more of modified forms of starch, calcium phosphate, a sugar e.g. lactose, microcrystalline cellulose and/or other directly compressible excipients, together with lubricant(s), e.g. stearic acid or magnesium stearate, flow aid(s), e.g. talc or colloidal silicon dioxide, and disintegrant(s), e.g. starch, substituted sodium carboxymethyl cellulose, cross linked sodium carboxy methyl cellulose, carboxy methyl starch and cross linked polyvinylpyrrolidone. Tablets are then formed by direct compression, and may be sugar or film coated e.g. with hydroxypropylmethylcellulose.

Alternatively the active ingredient may be granulated before tabletting. In such cases the active ingredient is mixed with one or more of starch, calcium phosphate, a sugar e.g. lactose, microcrystalline cellulose or other suitable excipients and granulated with a binder such as starch, pregelled starch, polyvinylpyrrolidone, gelatine, a modified gelatine, or a cellulose derivative, e.g. hydroxypropylmethylcellulose. The mass is then dried, sieved and mixed with lubricant(s), flow aid(s) and disintegrant(s), such as described in the previous paragraph. Tablets are then formed by compression of the granules, and may be sugar or film coated, e.g. with hydroxypropylmethylcellulose.

As a further alternative a powder, blend or granules, such as are described above as intermediates in tabletting, may be filled into a suitable, e.g. gelatine, capsule.

In order to improve the bioavailability, or decrease variability of availability, of the active ingredient the compound may be:

(a) dissolved in a suitable solvent, e.g. polyethylene glycol, Gelucaire, arachis oil, a (hydrogenated) vegetable oil or beeswax and the solution is then filled into a gelatine capsule, (b) produced as a spray-dried or freeze-dried form prior to mixing with other excipients, (c) milled and/or micronised to produce a powder with a large surface area prior to mixing with other excipients, (d) made into a solution and distributed over an inert excipient having a large surface area, e.g. colloidal silicon dioxide. The solvent is evaporated and further excipients added, (e) formed into a complex with cyclodextrin prior to mixing with other excipients. This complex also assists in increasing light stability, or (f) made into a solid solution or co-precipitated, e.g. with polyvinylpyrrolidone, polyethyleneglycol, modified cellulose, hydroxypropylmethylcellulose, urea or a sugar prior to mixing with further excipients.

The compounds, either in their normal form or in a modified form, e.g. as described immediately above, may be formulated in a controlled release form. Thus the compound may be dispersed, or contained in, a polymer matrix formed from, for example, ethylcellulose, hydroxypropylmethylcellulose or an acrylate/methacrylate polymer. Alternatively the compound may be formulated as a tablet or beads which are surrounded by a semi-permeable membrane, e.g. shellac, ethylcellulose or an acrylate/methacrylate polymer.

The compounds of this invention may be given in combination with other pharmaceutically active compounds, e.g. diuretics, beta-blockers, antihypertensives or inotropic agents. The dosage of the other pharmaceutically active compound can be that conventionally used when the compound is administered on its own, but is preferably somewhat lower. To illustrate these combinations, a compound of this invention effective in the range, e.g. 5–100 milligrams per day, can be combined at levels ranging, e.g. from 1–200 milligrams per day with the following beta-blockers, antihypertensives and diuretics in dose ranges per day as indicated: hydrochlorothiazide (15–200 mg), chlorothiazide (125–2000 mg), ethacrynic acid (15–100 mg), amiloride (5–20 mg), furosemide (5–80 mg), propanolol (20–480 mg), timolol (5–50 mg), captopril (10–500 mg), methyldopa (65–2000 mg) or digoxin (0.1–0.5 mg). In addition, the triple drug combinations of hydrochlorothiazide (15–200 mg) plus amiloride (5–20 mg) plus a compound of this invention (3–200 mg) and hydrochlorothiazide (15–200 mg) plus timolol (5–50 mg) plus a compound of this invention (3–200 mg), are provided. The above dose ranges may be adjusted on a unit basis as necessary to permit divided daily dosage. Also, the dose may vary depending on the severity of the disease, weight of patient and other factors which a person skilled in the art will recognise.

Certain of the compounds of formula I are assymetric and exhibit optical isomerism. Such compounds may be separated into their optical isomers using process p) or may be made by stereospecific syntheses using conventional techniques know per se.

The invention therefore provides the compounds as their individual optical isomers (we prefer the (+) isomers), and racemic or other mixtures of the individual isomers.

Certain of the compounds of the invention can form solvates, e.g. hydrates or alcoholates, and certain of the compounds are light sensitive and should therefore be produced, handled, stored and formulated in such a manner that they are not subjected to degrading amounts of light of the appropriate wavelengths.

The invention is illustrated, but in no way limited by the following Examples in which temperatures are in degress centigrade.

EXAMPLE 1

3-(Methyl) 5-(1-methylethyl)
4-(2,3-dichlorophenyl)-2-(fluoromethyl)-1,4-dihydro-6-methyl-3,5-pyridinedicarboxylate 2,3-Dichlorobenzaldehyde (1.75 g, 10 mmoles), methyl 4-fluoro-3-oxobutanoate (1.34 g, 10 mmoles) and 1-methylethyl 3-amino-2-butenoate (1.43 g, 10 mmoles) were heated with stirring at 90° for 2.5 hours. The reaction mixture was dissolved in ethyl acetate and chromatographed on silica eluting with petroleum ether (60°–80°)/ethyl acetate mixtures. Pure fractions were combined and evaporated to dryness. The title compound (1.6 g) was obtained by crystallisation from 2-propanol. mp 148°–9°.

EXAMPLE 2

3-Methyl 5-(1-methylethyl)
2-(fluoromethyl)-1,4-dihydro-6-methyl-4-(2-methyl-3-nitrophenyl)-3,5-pyridinedicarboxylate 2-Methyl-3-nitrobenzaldehyde (1.23 g, 7.5 mmoles), methyl 4-fluoro-3-oxobutanoate (1.0 g, 7.5 mmoles) and 1-methylethyl 3-amino-2-butenoate (1.07 g, 7.5 mmoles) were heated with stirring at 80° for 2.5 hours. The cooled residue was chromatographed twice on silica eluting first with ethyl acetate/petroleum ether (60°–80°) and then with ethyl acetate/methylene chloride. The title compound (0.61 g) was obtained by crystallisation from a mixture of petroleum ether (60°–80°) and 2-propanol mp 132°–133°.

EXAMPLE 3

5-Cyclopentyl 3-methyl
4-(2,3-dichlorophenyl)-2-(fluoromethyl)-1,4-dihydro-6-methyl-3,5-pyridinedicarboxylate 2,3-Dichlorobenzaldehyde (1.31 g, 7.5 mmoles), methyl 4-fluoro-3-oxobutanoate (1.0 g, 7.5 mmoles) and cyclopentyl 3-amino-2-butenoate (1.26 g, 7.5 mmoles) were heated at 90° with stirring under nitrogen for 2.5 hours. The reaction mixture was dissolved in ethyl acetate, dried (MgSO$_4$) and the solvent was removed in vacuo. The residue was chromatographed on silica eluting with ethyl acetate/methylene chloride mixtures. The title compound (0.95 g) was obtained after crystallisation from petroleum ether (60°–80) mp 148°–50°.

EXAMPLE 4

3-Methyl 5-(1-methylethyl)
4-(3-chloro-6-fluoro-2-(trifluoromethyl)phenyl)-2-(fluoromethyl)-1,4-dihydro-6-methyl-3,5-pyridinedicarboxylate 3-Chloro-6-fluoro-2-(trifluoromethyl)benzaldehyde (1.3 g, 5.7 mmoles), methyl 4-fluoro-3-oxobutanoate (0.77 g, 5.7 mmoles) and 1-methylethyl 3-amino-2-butenoate (0.82 g, 5.7 mmoles) were heated under nitrogen with stirring for 1.5 hours at 90°, followed by 1.5 hours at 100° and then 1 hour at 110°. The cooled reaction mixture was chromatographed twice on silica first using methylene chloride as eluent and then toluene/ethyl acetate mixtures. The title compound (0.2 g) was obtained after crystallisation from petroleum ether (60°–80°) mp 142°–3°.

EXAMPLE 5

3-Methyl 5-(1-methylethyl)
4-(2-chloro-3-nitrophenyl)-2-(fluoromethyl)-1,4-dihydro-6-methyl-3,5-pyridinedicarboxylate 2-Chloro-3-nitrobenzaldehyde (1.38 g, 7.5 mmoles), methyl 4-fluoro-3-oxobutanoate (1.0 g, 7.5 mmoles) and 1-methylethyl 3-amino-2-butenoate (1.06 g, 7.5 mmoles) were heated at 90° for 2.5 hours. The reaction mixture was chromatographed on silica eluting with petroleum ether (60°–80°)/ethyl acetate mixtures. The title compound (1.35 g) was obtained after crystallisation from petroleum ether (60°–80°)/2-propanol. mp 156°–7°.

EXAMPLE 6

3-Methyl 5-(1-methylethyl)
2-(fluoromethyl)-4-(2-fluoro-6-(trifluoromethyl)phenyl)-1,4-dihydro-6-methyl-3,5-pyridinedicarboxylate 2-Fluoro-6-(trifluoromethyl)benzaldehyde (1.51 g, 7.8 mmoles), methyl 4-fluoro-3-oxobutanoate (1.06 g, 7.8 mmoles) and 1-methylethyl 3-amino-2-butenoate (1.13 g, 7.8 mmoles) were heated at 90° under nitrogen with stirring for 2 hours. The cooled reaction mixture was chromatographed twice; first eluting with toluene/ethyl acetate mixtures and then with ethyl acetate/petroleum ether (60°–80°) mixtures. The title compound (0.1 g) was obtained on evaporation of the pure fractions mp 82°–4°.

EXAMPLE 7

3-Methyl 5-(1-methylethyl)
4-(2,3-dichloro-6-fluorophenyl)-2-(fluoromethyl)-1,4-dihydro-6-methyl-3,5-pyridinedicarboxylate 2,3-Dichloro-6-fluorobenzaldehyde (1.44 g, 7.5 mmoles), methyl 4-fluoro-3-oxobutanoate (1.0 g, 7.5 mmoles) and 1-methylethyl 3-amino-2-butenoate (1.06 g, 7.5 mmoles) were heated at 90° under nitrogen with stirring for 2.5 hours. The cooled reaction mixture was chromatographed on silica eluting with ethyl acetate/methylene chloride mixtures. The title compound (1.1 g) was obtained by crystallisation from a petroleum ether (60°–80°)/2-propanol mixture mp 129°–31°.

The compounds of Examples 8 to 49 were prepared using appropriate starting materials and the method described in Examples 1–7.

EXAMPLE 8

5-Ethyl 3-methyl
2-(fluoromethyl)-1,4-dihydro-6-methyl-4-(3-nitrophenyl)-3,5-pyridinedicarboxylate Recrystallised from 2-propanol. mp 127°–9°.

EXAMPLE 9

3-Methyl 5-(1-methylethyl)
2-(fluoromethyl)-1,4-dihydro-6-methyl-4-(3-nitrophenyl)-3,5-pyridinedicarboxylate Recrystallized from 2-propanol/cyclohexane. mp 107°–9°.

EXAMPLE 10

3-Methyl 5-(2-methylpropyl) 2-(fluoromethyl)-1,4-dihydro-6-methyl-4-(3-nitrophenyl)-3,5-pyridinedicarboxylate Recrystallized from 2-propanol/cyclohexane. mp 101°-2°.

EXAMPLE 11

3-Ethyl 5-methyl 2-(fluoromethyl)-1,4-dihydro-6-methyl-4-(3-nitrophenyl)-3,5-pyridinedicarboxylate Recrystallised from 2-propanol. mp 137°-8°.

EXAMPLE 12

Diethyl 2-(fluoromethyl)-1,4-dihydro-6-methyl-4-(2-(trifluoromethyl)phenyl)-3,5-pyridinedicarboxylate Crystallised from hexane. mp 84°-6°.

EXAMPLE 13

Diethyl 4-(4-benzofurazanyl)-2-(fluoromethyl)-1,4-dihydro-6-methyl-3,5-pyridinedicarboxylate Recrystallised from methylene chloride/cyclohexane. mp 125°-7°.

EXAMPLE 14

Dimethyl 2-(fluoromethyl)-1,4-dihydro-6-methyl-4-(2,3,4,5,6-pentafluorophenyl)-3,5-pyridinedicarboxylate Crystallised from cyclohexane. mp 148°-50°.

EXAMPLE 15

5-Methyl 3-(1-methylethyl) 2-(fluoromethyl)-1,4-dihydro-6-methyl-4-(3-nitrophenyl)-3,5-pyridinedicarboxylate Recrystallised from methylene chloride/cyclohexane. mp 122°-4°.

EXAMPLE 16

5-Ethyl 3-methyl 4-(2,3-dichlorophenyl)-2-(fluoromethyl)-1,4-dihydro-6-methyl-3,5-pyridinedicarboxylate Recrystallised from methylene chloride/cyclohexane. mp 124°-5°.

EXAMPLE 17

Diethyl 2-(fluoromethyl)-1,4-dihydro-6-methyl-4(2-(methylthio)-3-pyridyl)-3,5-pyridinedicarboxylate Recrystallised from cyclohexane/petroleum ether (60°-80°). mp 92°-4°.

EXAMPLE 18

3-Methyl 5-(2-(methyl(phenylmethyl)amino)ethyl) 2-(fluoromethyl)-1,4-dihydro-6-methyl-4-(3-nitrophenyl)-3,5pyridinedicarboxylate oxalate hemihydrate The purified free base was converted into the oxalate which was obtained as a yellow solid after trituration with ether, mp 95° with decomposition, softens at about 70°.

EXAMPLE 19

5-(2-Methoxyethyl) 3-(1-methylethyl) 4-(2,3-dichlorophenyl)-2-(fluoromethyl)-1,4-dihydro-6-methyl-3,5-pyridinedicarboxylate Recrystallised from cyclohexane/petroleum ether (60°-80°). mp 88°-9°.

EXAMPLE 20

5-(2-Cyanoethyl) 3-(1-methylethyl) 2-(fluoromethyl)-1,4-dihydro-6-methyl-4-(3-nitrophenyl)-3,5-pyridinedicarboxylate Recrystallised from 2-propanol. mp 231°-232.5°.

EXAMPLE 21

3-(1-Methylethyl) 5-(2-(methylthio)ethyl) 2-(fluoromethyl)-1,4-dihydro-6-methyl-4-(3-nitrophenyl)-3,5-pyridinedicarboxylate Recrystallised from 2-propanol/petroleum ether (60°-80°). mp 109°-111°.

EXAMPLE 22

3-Methyl 5-(1-methylethyl) 4-(2-chloro-5-nitrophenyl)-2-(fluoromethyl)-1,4-dihydro-6-methyl-3,5-pyridinedicarboxylate Recrystallised from 2-propanol/petroleum ether (60°-80°). mp. 131°-133°.

EXAMPLE 23

3-Ethyl 5-methyl 4-(2,3-dichlorophenyl)-2-(fluoromethyl)-1,4 dihydro-6-methyl-3,5-pyridinedicarboxylate Obtained as a solid by trituration with petroleum ether (60°-80°). mp 99°-101°.

EXAMPLE 24

3-Methyl 5-(1-methylethyl) 2-(fluoromethyl)-1,4-dihydro-6-methyl-4-(2-methyl-5-nitrophenyl)-3,5-pyridinedicarboxylate Recrystallised from 2-propanol/petroleum ether (60°-80°), mp 100°-1°.

EXAMPLE 25

3-(2-Methoxyethyl) 5-(1-methylethyl) 2-(fluoromethyl)-1,4-dihydro-6-methyl-4-(3-nitrophenyl)-3,5-pyridinedicarboxylate Recrystallised from cyclohexane as yellow crystals mp 112°-4°.

EXAMPLE 26

5-(2-Methoxyethyl) 3-(1-methylethyl) 2-(fluoromethyl)-1,4-dihydro-6-methyl-4-(3-nitrophenyl)-3,5-pyridinedicarboxylate Recrystallised from cyclohexane-isopropanol as a yellow solid mp 95°-6°.

EXAMPLE 27

3-Methyl 5-(1-methylethyl) 4-(2-chloro-3-(trifluoromethyl)phenyl)-2-(fluoromethyl)-1,4-dihydro-6-methyl-3,5-pyridinedicarboxylate Recrystallised from petroleum ether (60°-80°) mp 145°-7°.

EXAMPLE 28

5-(1-Methylethyl) 3-(tetrahydro-4H-pyran-4-yl) 2-(fluoromethyl)-1,4-dihydro-6-methyl-4-(3-nitrophenyl)-3,5-pyridinedicarboxylate Recrystallised from petroleum ether (60°-80°)/acetone, mp 128°-30°.

EXAMPLE 29

5-(1-Methylethyl) 3-(2-phenoxyethyl) 2-(fluoromethyl)-1,4-dihydro-6-methyl-4-(3-nitrophenyl)-3,5-pyridinedicarboxylate M+498; nmr (CDCl$_3$)δ6.6(d,NH), 5.1(s,H).

EXAMPLE 30

5-Methyl 3-(tetrahydro-4H-pyran-4-yl) 2-(fluoromethyl) 1,4-dihydro-6-methyl-4-(3-nitrophenyl)-3,5-pyridinedicarboxylate Yellow prisms (acetone/petroleum ether 60°-80°) mp 152°-4°.

EXAMPLE 31

5-Cyclohexyl 3-methyl 4-(2,3-dichlorophenyl)-2-(fluoromethyl)-1,4-dihydro-6-methyl-3,5-pyridinedicarboxylate Orange prisms (petroleum ether 60°-80°) mp 121°-3°.

EXAMPLE 32

5-Cyclopentyl 3-methyl 2-(fluoromethyl)-1,4-dihydro-6-methyl-4-(2-methyl-3-nitrophenyl)-3,5-pyridinedicarboxylate mp 167°-8°. (2-Propanol).

EXAMPLE 33

3-Methyl 5-(1-methylethyl) 4-(2,3-dimethoxyphenyl)-2-(fluoromethyl)-1,4-dihydro-6-methyl-3,5-pyridinedicarboxylate mp 89°-91°. (Petroleum ether 60°-80° /2-propanol).

EXAMPLE 34

3-Methyl 5-(tetrahydro-4H-pyran-4-yl) 4-(2,3-dichlorophenyl)-2-(fluoromethyl)-1,4-dihydro-6-methyl-3,5-pyridinedicarboxylate Orange prisms (acetone/petroleum ether 60°-80°) mp 143°-5°.

EXAMPLE 35

5-Cyclopentyl 3-methyl 2-(fluoromethyl)-1,4-dihydro-6-methyl-4-(2-(trifluoromethyl)phenyl)-3,5-pyridinedicarboxylate Yellow crystals (petroleum ether 40°-60°) mp 122°-3°.

EXAMPLE 36

5-Cyclopentyl 3-methyl 4-(3-chloro-6-fluoro-2-(trifluoromethyl)phenyl)-2-(fluoromethyl)-1,4-dihydro-6-methyl-3,5-pyridinedicarboxylate mp 184°-6°. (2-Propanol/petroleum ether 60°-80°).

EXAMPLE 37

5-(1-Ethylpropyl) 3 methyl 4-(2,3-dichlorophenyl)-2-(fluoromethyl)-1,4-dihydro-6-methyl-3,5-pyridinedicarboxylate Pale yellow prisms (petroleum ether 40°-60°) mp 118°-9°.

EXAMPLE 38

3-Methyl 5-(1-methylethyl) 2-(fluoromethyl)-1,4-dihydro-4-(2-methoxy-3-nitrophenyl)-6-methyl-3,5-pyridinedicarboxylate mp 105°-6°. (2-Propanol/petroleum ether 60°-80°).

EXAMPLE 39

3-Methyl 5-(1-methylethyl) 2-(fluoromethyl)-1,4-dihydro-6-methyl-4-(2-(trifluoromethyl)phenyl)-3,5-pyridinedicarboxylate Pale yellow crystals (hexane) mp 71°-2°.

EXAMPLE 40

3-Methyl 5-(1-methylethyl) 2-(fluoromethyl)-1,4-dihydro-6-methyl-4-(2-nitrophenyl)-3,5-pyridinedicarboxylate Yellow crystals (petroleum ether 60°-80°) mp 142°-3°.

EXAMPLE 41

3-Methyl 5-(1-methylethyl) 2-(fluoromethyl)-4-(2-fluorophenyl)-1,4-dihydro-6-methyl-3,5-pyridinedicarboxylate Yellow crystals (petroleum ether 60°-80°) mp 129°-31°.

EXAMPLE 42

3-Methyl 5-(1-methylethyl) 2-(fluoromethyl)-1,4-dihydro-6-methyl-4-(2-methylphenyl)-3,5-pyridinedicarboxylate Pale yellow crystals (petroleum ether 60°-80°) mp 94°-5°.

EXAMPLE 43

3-Methyl 5-(1-methylethyl) 4-(2-chlorophenyl)-2-(fluoromethyl)-1,4-dihydro-6-methyl-3,5-pyridinecarboxylate Yellow crystals (petroleum ether 60°-80°) mp 137°-9°.

EXAMPLE 44

3-Methyl 5-(1-methylethyl) 2-(fluoromethyl)-1,4-dihydro-6-methyl-4-(2-(methylthio)phenyl)-3,5-pyridinedicarboxylate

EXAMPLE 45

3-Methyl 5-(1-methylethyl) 2-(fluoromethyl)-1,4-dihydro-6-methyl-4-(2-(methylsulphonyl)phenyl)-3,5-pyridinedicarboxylate

EXAMPLE 46

3-Methyl 5-(1-methylethyl) 4-(3-chloro-2-methylphenyl) -2-(fluoromethyl)-1,4-dihydro-6-methyl-3,5-pyridinedicarboxylate mp 73°-5° (cyclohexane).

EXAMPLE 47

3-Methyl 5-(1-methylethyl) 4-(2,3-dimethylphenyl)-2-(fluoromethyl)-1,4-dihydro-6-methyl-3,5-pyridinedicarboxylate

EXAMPLE 48

3-Methyl 5-(1-methylethyl) 4-(3-cyanophenyl)-2-(fluoromethyl)-1,4-dihydro-6-methyl-3,5-pyridinedicarboxylate Pale yellow crystals (2-propanol/petroleum ether 60°–80°) mp 117°–8°.

EXAMPLE 49

3-Methyl 5-(1-methylethyl) 4-(3-chlorophenyl)-2-(fluoromethyl)-1,4-dihydro-6-methyl-3,5-pyridinedicarboxylate Pale yellow crystals (petroleum ether 60°–80°) mp 107°–9°.

EXAMPLE 50

5-Cyclopentyl 3-methyl 4-(2,3-dichlorophenyl)-2-(fluoromethyl)-1,4-dihydro-6-methyl-3,5-pyridinedicarboxylate (a) Cyclopentyl 2-(2,3-dichlorophenylmethylene)-3-oxobutanoate A solution of 2,3-dichlorobenzaldehyde (2.5 g, 14.3 mmoles), cyclopentyl 3-oxobutanoate (2.42 g, 14.3 mmoles), piperidine (8 drops) and hexanoic acid (11 drops) in dry benzene (80 ml) was heated at reflux for 4 hours using a Dean and Stark apparatus. The solution was allowed to cool to room temperature and the solvent removed in vacuo to leave the sub-title compound as an oil 5.1 g.

(b) A solution of the product of step (a) (5.1 g, 14.3 mmoles) and methyl 3-amino-4-fluoro-2-butenoate (1.9 g, 14.3 mmoles) in dry tert-butanol (25 ml) was heated to 60° (oil bath temperature) for 108 hours. The solution was allowed to cool to room temperature and the solvent removed in vacuo. Chromatography on silica eluting with dichloromethane afforded the title compound as a yellow oil which crystallises on addition of petroleum ether (60°–80°) to afford the title compound 1.5 g mp 148°–9°. (Identical with the product of Example 3).

EXAMPLE 51

5-Cyclobutyl 3-methyl 4-(2,3-dichlorophenyl)-2-(fluoromethyl)-1,4-dihydro-6-methyl-3,5-pyridinedicarboxylate (a) Cyclobutyl 2-(2,3-dichlorophenylmethylene)-3-oxobutanoate A solution of 2,3-dichlorobenzaldehyde (1.57 g, 8.9 mmoles), cyclobutyl 3-oxobutanoate (1.4 g, 8.9 mmoles), piperidine (8 drops) and hexanoic acid (11 drops) in dry benzene (100 ml) was heated at reflux for 12 hours using a Dean and Stark apparatus. The solution was allowed to cool to room temperature and the solvent removed in vacuo to leave the crude sub-title compound as an oil 3.5 g. Chromatography on silica eluting with petroleum ether (60°–80°)/ethyl acetate mixtures afforded the sub-title compound as an oil, 1.7 g.

(b) The product of step (a) (1.7 g, 5.4 mmoles) and methyl 3-amino-4-fluoro-2-butenoate (0.72 g, 5.4 mmoles) were mixed and heated to 95° (oil bath temperature) under an atmosphere of nitrogen for 6 hours. The oil was allowed to cool to room temperature. Chromatography on silica eluting with petroleum ether (60°–80°)/ethyl acetate mixtures, afforded the title compound as a yellow solid, which was recrystallised from petroleum ether (60°–80°) to afford the title compound 0.37 g, mp 148°–9°.

EXAMPLE 52

3-Methyl 5-(3-oxetanyl) 4-(2,3-dichlorophenyl)-2-(fluoromethyl)-1,4-dihydro-6-methyl-3,5-pyridinedicarboxylate (a) (3-Oxetanyl) 2-(2,3-dichlorophenylmethylene)-3-oxobutanoate A solution of 2,3-dichlorobenzaldehyde (1.33 g, 7.6 mmoles), 3-oxetanyl 3-oxobutanoate (1.2 g, 7.6 mmoles), piperidine (6 drops) and hexanoic acid (8 drops) in dry benzene (80 ml) was heated at reflux using a Dean and Stark apparatus. The solution was allowed to cool to room temperature and the solvent removed in vacuo to leave the sub-title compound as an oil 2.9 g.

(b) A solution of the product of step (a) (2.9 g, 7.6 mmoles) and methyl 3-amino-4-fluoro-2-butenoate (1g, 7.6 mmoles) in dry tert-butanol (20 ml) was heated to 60° (oil bath temperature) for 16 hours. The solution was allowed to cool to room temperature and the solvent removed in vacuo. Chromatography on silica, eluting with dichloromethane/ethyl acetate mixtures afforded the title compound as an oil which crystallised on addition of petroleum ether (60°–80°). The solid was recrystallised from petroleum ether (60°–80°)/acetone to afford the title compound 1.03 g, mp 155°–6°.

EXAMPLE 53

3-Methyl 5-((S)-2,2,2-trichloro 1-phenylethyl) 4-(2,3-dichlorophenyl)-2-(fluoromethyl)-1,4-dihydro-6-methyl-3,5-pyridinedicarboxylate (a) (S)-2,2,2-Trichloro-1-phenylethyl 2-(2,3-dichlorophenylmethylene)-3-oxobutanoate (S)-2,2-Trichloro-1-phenylethyl 3-oxobutanoate (8.6 g 27.5 mmoles) and 2,3-dichlorobenzaldehyde (4.82 g, 27.5 mmoles) in dry benzene (100 ml) were heated at reflux for 5 hours with hexanoic acid (25 drops) and piperidine (8 drops) in a Dean and Stark apparatus. The solvent was evaporated and the residue dissolved in ethyl acetate (200 ml), washed with saturated sodium bicarbonate, 2% aqueous sodium bisulphite solution and brine, dried (MgSO$_4$) and the solvent removed in vacuo. The sub-title compound was obtained as a yellow oil. HPLC and nmr indicate 2:1 mixture of geometric isomers.

(b) 3-Methyl 5-((S)-2,2,2-trichloro-1-phenylethyl) 4-(2,3-dichlorophenyl)-2-(fluoromethyl)-1,4-dihydro-6-methyl-3,5-pyridinedicarboxylate Single diastereomers A and B (S)-2,2,2-Trichloro-1-phenylethyl 2-(2,3-dichlorophenylmethylene)-3-oxobutanoate (10.8 g, 23 mmoles) and methyl 3-amino-4-fluoro-2-butenoate (3.7 g, 28 mmoles) were heated at 55° in dry tert-butanol (50 ml) for 68 hours. The solvent was removed and the residue purified and separated into single diastereomers by HPLC eluting with methylene chloride/petroleum ether (60°–80°) mixtures.

First eluted: diastereomer A, recrystallised from cyclohexane/petroleum ether (60°–80°) mp 167.5°–8° $[\alpha]_D^{25}$ +17.5° (c, 0.1 in ethanol).

Second eluted diastereomer B, recrystallised from petroleum ether (60°-80°) mp 141°-3° $[\alpha]_D^{25}$ −150.1° (c, 0.1 in ethanol).

EXAMPLE 54

3-Methyl 5-(2,2,2-trichloro-1-phenylethyl) 4-(2,3-dichlorophenyl)-2-(fluoromethyl)-1,4-dihydro-6-methyl-3,5-pyridinedicarboxylate Diastereomeric pairs A and B Prepared by the method of Example 53 and separated by HPLC using methylene chloride/petroleum ether (60°-80°) mixtures.

First eluted: diastereomeric pair A. Recrystallised from cyclohexane/petroleum ether (60°-80°) mp 203°-4°.

Second eluted: diastereomeric pair B. Recrystallised from cyclohexane/petroleum ether (60°-80°) mp 176°-176.5°.

The compounds of Examples 55 to 64 were prepared using appropriate starting materials and the method described in Examples 50-54.

EXAMPLE 55

Diethyl 2-(difluoromethyl)-1,4-dihydro-6-methyl-4-(3-nitrophenyl)-3,5-pyridinedicarboxylate mp 148°-9° (2-propanol).

EXAMPLE 56

Diethyl 1,4-dihydro-2-methyl-6-methylthio-4-(3-nitrophenyl)-3,5-pyridinedicarboxylate mp 123°-5° (2-propanol).

EXAMPLE 57

Diethyl 1,4-dihydro-2-(4-methoxyphenyl)-6-methyl-4-(3-nitrophenyl)-3,5-pyridinedicarboxylate mp 166°-7° (2-Propanol).

EXAMPLE 58

Diethyl 2-(dichloromethyl)-1,4-dihydro-6-methyl-4-(3-nitrophenyl)-3,5-pyridinedicarboxylate Recrystallised from isopropanol as yellow crystals mp 139°-141°.

EXAMPLE 59

5-(1-(Diphenylmethyl)-3-azetidinyl) 3-methyl 4-(2,3-dichlorophenyl)-2-(fluoromethyl)-1,4-dihydro-6-methyl-3,5-pyridinedicarboxylate Pale yellow solid (petroleum ether 60°-80°) mp 163°-5°.

EXAMPLE 60

3-Methyl 5-(1-(phenylmethyl)-4-piperidinyl) 4-(2,3-dichlorophenyl)-2-(fluoromethyl)-1,4-dihydro-6-methyl-3,5-pyridinedicarboxylate Pale yellow solid. mp 118°-20°.

EXAMPLE 61

5-(1,1-Dimethylethyl) 3-methyl 4-(2,3-dichlorophenyl)-2-(fluoromethyl)-1,4-dihydro-6-methyl-3,5-pyridinedicarboxylate Pale yellow solid (petroleum ether 60°-80°) mp 141°.

EXAMPLE 62

3-Methyl 5-(1-methyl-1-phenylethyl) 4-(2,3-dichlorophenyl)-2-(fluoromethyl)-1,4-dihydro-6-methyl-3,5-pridinedicarboxylate Colourless solid (acetone-petroleum ether 60°-80°). mp 173°-5°.

EXAMPLE 63

3-Methyl 5-(1-methylcyclopentyl) 4-(2,3-dichlorophenyl)-2-(fluoromethyl)-1,4-dihydro-6-methyl-3,5-pyridinedicarboxylate Colourless solid (petroleum ether 60°-80°). mp 111°.

EXAMPLE 64

3-Methyl 5-(2,2,2-trichloro-1-phenylethyl) 2-(fluoromethyl)-1,4-dihydro-6-methyl-4-(3-nitrophenyl)-3,5-pyridinedicarboxylate Diastereomers obtained as yellow foam. M+562/560/558/556. Nmr (CDCl$_3$)δ5.24 and 5.26 (2xs,1H), 6.32 and 6.34 (2xs,1H).

EXAMPLE 65

Diethyl 1,4-dihydro-2-methyl-4-(3-nitrophenyl)-6-(4-nitrophenyl)-3,5-pyridinedicarboxylate Trifluoroacetic anhydride (0.65 ml, 4.63 mmoles) was added with stirring to pyridine (0.75 ml, 9.26 mmoles) and diethyl 1,2,3,4-tetrahydro-2-hydroxy-6-methyl-4-(3-nitrophenyl)-2-(4-nitrophenyl)-3,5-pyridinedicarboxylate (2.31 g, 4.63 mmoles) in methylene chloride (60 ml). After stirring for 2.5 hours, the solution was washed with water, dilute hydrochloric acid (x3), water, saturated sodium bicarbonate solution, water and dried (Na$_2$SO$_4$). The solvent was removed in vacuo and the residue recrystallised from ethanol to give the title compound (1.77 g) as a yellow solid, mp 176°-7°.

The compounds of Examples 66 to 71 were prepared using appropriate starting materials and the method of Example 65.

EXAMPLE 66

Diethyl 2-(3,4-dichlorophenyl)-1,4-dihydro-6-methyl-4-(3-nitrophenyl)-3,5-pyridinedicarboxylate Yellow solid mp 153°-6° (ethanol).

EXAMPLE 67

Diethyl 2-(4-chlorophenyl)-1,4-dihydro-6-methyl-4-(3-nitrophenyl)-3,5-pyridinedicarboxylate Yellow solid mp 158°-60° (ethanol).

EXAMPLE 68

Diethyl 1,4-dihydro-2-methyl-4-(3-nitrophenyl)-6-(trifluoromethyl)-3,5-pyridinedicarboxylate Yellow solid mp 93°-5° (ether-petroleum ether 60°-80°).

EXAMPLE 69

Diethyl 2-(3-chlorophenyl)-1,4-dihydro-6-methyl-3-nitrophenyl)-3,5-pyridinedicarboxylate Recrystallised from 2-propanol. mp 160°-1°.

EXAMPLE 70

Diethyl 1,4-dihydro-2-methyl-4-(3-nitrophenyl)-6(pentafluoroethyl)-3,5-pyridinedicarboxylate Obtained pure after chromatography. mp 88°–9°.

EXAMPLE 71

5-Ethyl 3-methyl 4-(2,3-dichlorophenyl)-1,4-dihydro 2-methyl-6-(trifluoromethyl)-3,5-pyridinedicarboxylate Recrystallised from cyclohexane, mp 101°–2°.

EXAMPLE 72

Diethyl 1,4-dihydro-2-methyl-4-(3-nitrophenyl)-6-(trichloromethyl)-3,5-pyridinedicarboxylate (a) Diethyl 3,4-dihydro-2-methyl-4-(3-nitrophenyl)-6-(trichloromethyl)-3,5-pyridinedicarboxylate Diethyl 1,2,3,4-tetrahydro-2-hydroxy-6-methyl-4-((3-nitrophenyl)-2-(trichloromethyl)-3,5-pyridinedicarboxylate (3.0 g, 6.05 mmoles) was dissolved in dry methylene chloride (150 ml) and diethylaminosulphur trifluoride (1.5 ml) was added. After 1 hour the solution was diluted with methylene chloride and washed in turn with dilute hydrochloric acid and saturated sodium bicarbonate solution. After drying (MgSO$_4$), the solvent was removed in vacuo to give the sub-title compound (2.82 g) as an oil. Nmr (D$_6$-DMSO)δ4.8 (s,H), 4.4 (s,H).

(b) Diethyl 1,4-dihydro-2-methyl-4-(3-nitrophenyl)-6-(trichloromethyl)-3,5-pyridinedicarboxylate The product of step (a) (2.67 g) was dissolved in methylene chloride (20 ml) and triethylamine (0.5 ml) was added. After 18 days at room temperature, the solvent was evaporated and the residue chromatographed on silica eluting with methylene chloride. The title compound (0.65 g) was obtained after crystallisation from 2-propanol mp 113°–5°. Nmr (D$_6$-DMSO)δ9.0 (s,H), 4.9 (s,H).

EXAMPLE 73

Diethyl 1,4-dihy-dro-2-methyl-6-(methylsulphinyl)-4-(3-nitrophenyl)-3,5-pyridinedicarboxylate Isomers I and II Peracetic acid (6.8 ml of 1M solution in methanol) was added to a solution of diethyl 1,4-dihydro-2-methyl-6-(methylthio)-4-(3-nitrophenyl)-3,5-pyridinedicarboxylate (2.77 g 6.8 mmoles) in methylene chloride (150 ml) at −78°. The reaction mixture was allowed to reach room temperature and was then stirred for 30 minutes. Saturated aqueous sodium bicarbonate (150 ml) was added and the organic layer separated, dried (Na$_2$SO$_4$) and the solvent removed in vacuo. The residue was chromatographed on silica, eluting with ether/petroleum ether (60°–80°) mixtures. The two isomers were separated and recrystallised from 2-propanol.

Diastereomer I yellow crystals mp 143°–4° (0.84 g).
Diastereomer II yellow crystals mp 133°–5° (1.25 g).

EXAMPLE 74

Diethyl 2-aminocarbonyl-1,4-dihydro-6-methyl-4-(3-nitrophenyl)-3,5-pyridinedicarboxylate A solution of 3,5-diethyl 1,4-dihydro-6-methyl-4-(3-nitrophenyl)-2,3,5-pyridinetricarboxylate (4.0 g; 10.3 mmoles), 1,1'-carbonyldiimidazole (1.75 g; 10.8 mmoles) in dry dichloromethane (180 ml) was stirred at room temperature under an atmosphere of dry nitrogen. After 2 hours a yellow suspension had formed, ammonia solution (20 ml, d=0.88) was added and the 2-phase mixture left stirring for 16 hours.

Saturated brine (100 ml) was added, the organic solution was separated, washed with 15% aq. sodium hydroxide solution, saturated brine, water and dried (MgSO$_4$).

Evaporation of the solvent was followed by chromatography o silica (150 g) using ethyl acetate/petroleum ether (60°–80°) as eluent.

The title compound was obtained as a white solid which was recrystallised from 2-propanol to give a white powder (0.8 g) mp 166°–8°.

EXAMPLE 75

Diethyl 2-(dimethylaminocarbonyl)-1,4-dihydro-6-methyl-4-(3-nitrophenyl)-3,5-pyridinedicarboxylate Thionyl chloride (0.05 ml) was added to a solution of 3,5-diethyl 1,4-dihydro-6-methyl-4-(3-nitrophenyl)-2,3,5pyridinetricarboxylate (0.25 g, 0.62 mmoles) in methylene chloride (10 ml) containing dimethylformamide (1 drop). After 2 hours at room temperature further thionyl chloride (0.05 ml) was added and the solution was refluxed for 30 mins. After cooling to room temperature 10% dimethylamine in benzene (1 ml) was added and the mixture stirred for 30 mins. The solvent was evaporated and the residue dissolved in dilute hydrochloric acid and ether. The organic extract was washed with brine, dried (Na$_2$SO$_4$) and the solvent removed in vacuo to leave the title compound (0.2 g). M+431; nmr (CDCl$_3$)δ5.12 (s,H), 3.05 (s,3H), 2.95 (s,3H).

EXAMPLE 76

Diethyl 1,4-dihydro-2-(1H-imidazol-1-ylcarbonyl)-6-methyl-4-(3-nitrophenyl)-3,5-pyridinedicarboxylate and Diethyl 1,4-dihydro-2-methyl-6-(4-morpholinylcarbonyl)-4-(3-nitrophenyl)-3,5-pyridinedicarboxylate A solution of 3,5-diethyl 1,4-dihydro-6-methyl-4-(3-nitrophenyl)-2,3,5-pyridinetricarboxylate (2.5 g, 6.2 mmoles) and 1,1'-carbonyldiimidazole (1.2 g, 7.4 mmoles) in methylene chloride (100 ml) was stirred at room temperature for 4 hours. Morpholine (1.08 ml, 12.4 mmoles) was added, the mixture stirred overnight and then poured onto 10% hydrochloric acid. The organic layer was separated, washed with 10% hydrochloric acid, brine, saturated sodium bicarbonate, brine and dried (Na$_2$SO$_4$). The solvent was evaporated and the residue chromatographed on silica eluting with ethyl acetate/petroleum ether (60°–80°) mixtures. The imidazolyl-carbonyl (0.24 g) compound was eluted first (M+454).

Further elution afforded the morpholinylcarbonyl compound (0.4 g) (M+473).

EXAMPLE 77

Diethyl 2-(aminothioxomethyl)-1,4-dihydro-6-methyl-4-(3-nitrophenyl)-3,5-pyridinedicarboxylate Hydrogen sulphide was bubbled through a solution of diethyl 2-cyano-1,4-dihydro-6-methyl-4-(3-nitrophenyl)-3,5-pyridinedicarboxylate (1g, 2.6 mmoles) in triethylamine (0.36 ml, 2.6 mmoles) and pyridine (20 ml) at room temperature for 2 hours. The solution was degassed with nitrogen and poured into water (300 ml). After stirring for 2 hours, the precipitate was filtered off, dissolved in methylene chloride and dried (Na$_2$SO$_4$). The solvent was removed in vacuo and the residue triturated with CCl$_4$ and filtered to give the title compound (0.5 g). M$^+$419; (CDCl$_3$)δ9.3 (s,NH$_2$), 5.2 (s,H).

EXAMPLE 78

Diethyl 1,4-dihydro-2-(imino(methylthio)methyl)-6-methyl-4-(3-nitrophenyl)-3,5-pyridinedicarboxylate hydroiodide Methyl iodide (0.06 ml, 0.96 mmoles) was added to a solution of diethyl 2-(aminothioxomethyl)-1,4-dihydro-6-methyl-4-(3-nitrophenyl)-3,5-pyridinedicarboxylate (0.2 g, 0.48 mmoles) in methanol (10 ml). After stirring for 16 hours at room temperature methyl iodide (0.1 ml) was added and the stirring continued for 1 day. The solvent was evaporated and the residue crystallised on addition of ether. The hydroscopic solid was filtered and dried in vacuo to give the title compound (0.17 g). Nmr (CDCl$_3$)δ5.9 (s,H), 2.9 (s,SMe).

EXAMPLE 79

Diethyl 2-(fluoromethyl)-1,4-dihydro-6-methyl-4-(3-nitrophenyl)-3,5-pyridinedicarboxylate Ethyl 4-fluoro-3-oxobutanoate (1.45 g, 10 mmoles), ethyl 2-(3-nitrophenylmethylene)-3-oxobutanoate (2.63 g, 10 mmoles) and aqueous ammonia (1.1 ml, d 0.88) were heated at reflux in ethanol (15 ml) for 6 hours. The solvent was removed in vacuo and the residue purified by chromatography on silica eluting with petroleum ether (60°–80° )/ether mixtures. Recrystallisation from ether/petroleum ether (60°–80° ) gave the title compound (1.1 g) as yellow crystals mp 139°–41°.

The compounds of Examples 80 to 82 were prepared using appropriate starting materials and the method of Example 79.

EXAMPLE 80

Di-(2-propoxyethyl) 2-(fluoromethyl)-1,4-dihydro-6-methyl-4-(3-nitrophenyl)-3,5-pyridinedicarboxylate Recrystallised from ether-hexane as a yellow solid mp 52°–3°.

EXAMPLE 81

Diethyl 1,4-dihydro-2-methyl-6-(4-methylphenyl)-4-(3-nitrophenyl)-3,5-pyridinedicarboxylate mp 149°–50° . (Ethanol).

EXAMPLE 82

Diethyl 2-(2-furanyl)-1,4-dihydro-6-methyl-4-(3-nitrophenyl)-3,5-pyridinedicarboxylate mp 130°–1° (2-propanol).

EXAMPLE 83

3-Methyl 5-(1-methylethyl) 2-(difluoromethyl)-1,4-dihydro-6-methyl-4-(3-nitrophenyl)-3,5-pyridinedicarboxylate Diethylaminosulphur trifluoride (0.64 ml, 5.1 mmoles) was added to a stirred solution at −10° of 3-methyl -(1-methylethyl) 2-formyl-1,4-dihydro-6-methyl-4-(3-nitrophenyl)-3,5-pyridinedicarboxylate (2 g, 5.2 mmoles) in dry methylene chloride (20 ml). After stirring for 2 hours at −10° and 1 hr at room temperature, diethylaminosulphur trifluoride (0.2 ml) was added and the stirring continued for a further hour. The reaction mixture was poured into aqueous sodium bicarbonate (100 ml) and extracted with methylene chloride (2×100 ml). The organic extracts were washed with water (2×) and brine, dried (MgSO$_4$) and the solvent was evaporated. Chromatography on silica eluting with ethyl acetate/petroleum ether (60°–80° ) mixtures, followed by crystallisation from 2-propanol gave the title compound (0.57 g). mp 140°–1°.

EXAMPLE 84

5-Cyclopentyl 3-methyl 2-(difluoromethyl)-1,4-dihydro-6-methyl-4-(2-methyl-3-nitrophenyl)-3,5-pyridinedicarboxylate 5-Cyclopentyl 3-methyl 2-formyl-1,4-dihydro-6-methyl-4-(2-methyl-3-nitrophenyl)-3,5-pyridinedicarboxylate (0.62 g, 1.45 mmoles) was dissolved in dry methylene chloride (6 ml) and then cooled to 0°. Diethylaminosulphur trifluoride (180 µl, 1.45 mmoles) was added and the reaction mixture stirred at room temperature for 4 hours. The solvent was removed in vacuo and the residue chromatographed on silica eluting with ether/petroleum ether (60°–80° ) mixtures. The title compound (0.22 g) was obtained on evaporation of pure fractions mp 154°–6°.

EXAMPLE 85

3-Methyl 5-(1-methylethyl) 4-(2,3-dichlorophenyl)-2-(difluoromethyl)-1,4-dihydro-6-methyl-3,5-pyridinedicarboxylate 3-Methyl 5-(1-methylethyl) 4-(2,3-dichlorophenyl)-2-formyl-1,4-dihydro-6-methyl-3,5-pyridinedicarboxylate (1.5 g, 3.6 mmoles) was dissolved in dry methylene chloride (20 ml) and cooled to −60°. Diethylaminosulphur trifluoride (0.59 g, 3.6 mmoles) was added and the stirred mixture was allowed to reach room temperature. After 2 hours, the solvent was removed in vacuo and the residue chromatographed on silica eluting with methylene chloride/ethyl acetate mixtures. The title compound (0.6 g) was obtained, after crystallisation from 2-propanol. mp 156°–7°.

EXAMPLE 86

Diethyl 2-(fluoromethyl)-1,4-dihydro-6-methyl-4-(3-nitrophenyl)-3,5-pyridinedicarboxylate Diethyl 1,4-dihydro-2-(hydroxymethyl)-6-methyl-4-(3-nitrophenyl)-3,5-pyridinedicarboxylate (0.1 g, 0.25 mmoles) in dry methylene chloride (5 ml) was added to a stirred solution at −60° of diethylaminosulphur trifluoride (0.068 ml, 0.55 mmoles) in dry methylene chloride (10 ml) over 10 minutes. The reaction mixture was allowed to reach room temperature over 2.5 hours, poured into aqeuous sodium bicarbonate (15 ml) and the aqueous layer extracted with methylene chloride (2×). The organic extracts were washed with water, dried (MgSO$_4$) and the solvent was evaporated. The residue was chromatographed on silica eluting with ethyl acetate/methylene chloride mixtures to give the title compound (0.015 g); identical with that prepared in Example 94.

The compounds of Examples 87 and 88 were prepared using appropriate starting materials and the method described in Examples 83–85.

EXAMPLE 87

3-(2-Methoxyethyl) 5-(1-methylethyl) 4-(2,3-dichlorophenyl)-2-(difluoromethyl)-1,4-dihydro-6-methyl-3,5-pyridinedicarboxylate mp. 127°–128°. (2-Propanol).

EXAMPLE 88

3-(2-Methoxyethyl) 5-(1-methylethyl) 2-(difluoromethyl)-1,4-dihydro-6-methyl-4-(3-nitrophenyl)-3,5-pyridinedicarboxylate mp 146°–7°. (2-Propanol).

EXAMPLE 89

(+) 3-Methyl 5-(1-methylethyl) 4-(2,3-dichlorophenyl)-2-(fluoromethyl)-1,4-dihydro-6-methyl-3,5- pyridinedicarboxylate Diastereomer A (0.58 g, from Example 53) was dissolved in acetonitrile (6 ml) and formic acid (0.19 ml) and zinc dust (0.6 g) were added in turn. The reaction mixture was stirred for 2.5 hours and then cooled in ice while chloroform (20 ml) and water (20 ml) were added. The aqueous layer was acidified with dilute hydrochloric acid; the organic layer was separated and the aqueous layer re-extracted with chloroform. The combined organic extracts were dried (Na$_2$SO$_4$) and the solvent removed in vacuo to afford 3-methyl 4-(2,3-dichlorophenyl)-2-(fluoromethyl)-1,4-dihydro-6-methyl-3,5-pyridinedicarboxylate.

The mono-acid was azeotroped once with carbon tetrachloride and then dissolved in ethyl acetate (10 ml). 2-Propanol (0.7 ml) and dicyclohexylcarbodiimide (1.75 g) were added and the mixture stirred at room temperature overnight and then heated at 60° for 2 hours. The solvent was removed in vacuo and the residue chromatographed on silica eluting with methylene chloride, followed by recrystallisation from hexane, to give the title compound (0.2 g) mp 124°–5° [α]$_D^{24.5}$+38.2° (c 0.1 in ethanol).

EXAMPLE 90

(−) 3-Methyl 5-(1-methylethyl) 4-(2,3-dichlorophenyl)-2-(fluoromethyl)-1,4-dihydro-6-methyl-3,5-pyridinedicarboxylate Prepared as in Example 89, using diastereomer B from Example 53. Recrystallised from methanol/hexane mp 124°–5° [α]$_D^{24}$−42.3° (c 0.11 in ethanol).

EXAMPLE 91

(+) 5-Cyclopentyl 3-methyl 4-(2,3-dichlorophenyl)-2-(fluoromethyl)-1,4-dihydro-6-methyl-3,5-pyridinedicarboxylate Prepared as in Example 89, using diastereomer A from Example 53 and esterifying with cyclopentanol. Recrystallised from hexane mp 89°–91°, [α]$_D^{24.5}$+62.9° (c 0.1 in ethanol).

EXAMPLE 92

(−) 5-Cyclopentyl 3-methyl 4-(2,3-dichlorophenyl)-2-(fluoromethyl)-1,4-dihydro-6-methyl-3,5-pyridinedicarboxylate Prepared as in Example 91, using diastereomer B from Example 53 and esterifying with cyclopentanol.

EXAMPLES OF INTERMEDIATES

Example A

Methyl 4-fluoro-3-oxo-butanoate

Fluoroacetyl chloride (7.1 g, 73 mmoles) was added dropwise to a stirred solution of 2,2-dimethyl-1,3-dioxane-4,6-dione (10.65 g, 74 mmoles) and pyridine (16.85 ml, 210 mmoles) in methylene chloride (75 ml) keeping the temperature below 10°. After stirring for 16 hours at room temperature the solution was diluted with methylene chloride (100 ml) and then washed with 1N hydrochloric acid (200 ml) and water (100 ml). The organic extract was dried (Na$_2$SO$_4$) and the solvent removed in vacuo. The residue was dissolved in methanol (150 ml) and the solution heated at reflux for 2.5 hours. Removal of the solvent followed by distillation at 60°–80° (bath temp)/14 mm Hg gave methyl 4-fluoro-3-oxobutanoate (6.4 g).

The compounds of Examples B and C were prepared using appropriate starting materials and the method of Example A.

Example B

1-Methylethyl 4-fluoro-3-oxobutanoate

Colourless oil, bp 100°–120° (bath temp)/12 mm Hg.

Example C

Tetrahydro-4H-pyran-4-yl 4-fluoro-3-oxobutanoate

Nmr (CDCl$_3$) δ5.0(m,H), 4.9(d,2H,J=48 Hz).

Example D

2-Methoxyethyl 4-fluoro-3-oxobutanoate

Ethyl 4-fluoro-3-oxobutanoate (2.1 g) was heated at reflux in 2-methoxyethanol (10ml) for 3 hours. The solvent was removed in vacuo and the residue distilled to give the title compound as a colourless oil (1.75 g). Nmr (CDCl$_3$)δ4.9 (d,2H,J-48 Hz), 3.4 (s,3H).

The compounds of Examples E and F were prepared using appropriate starting materials and the method of Example D.

Example E

2-Propoxyethyl 4-fluoro-3-oxobutanoate

Nmr (CDCl$_3$)δ4.9 (d,2H,J=47 Hz), 0.9 (t,3H,J=7 Hz).

Example F

2-Phenoxyethyl 4-fluoro-3-oxobutanoate

Nmr (CDCl$_3$)δ7.5–6.9 (m,5H), (4.9 d,2H,J=48 Hz).

Example G

Methyl 3-amino-4-fluoro-2-butenoate

Ammonia was bubbled through a solution of methyl 4-fluoro-3-oxobutanoate (2.6 g) in methanol (26 ml) at 0° for 3 hours. After stirring overnight at room temperature the solvent was removed in vacuo and the residue distilled (bp 100° at 20 mm Hg) to give the title compound (1.3 g) Nmr (CDCl₃) 4.9 (d,2H,J=48 Hz), 4.6 (s,H), (3.7 s,3H).

The compounds of Examples H to J were prepared using appropriate starting materials and the method of Example G.

Example H

Ethyl 3-amino-4-fluoro-2-butenoate

M+147; nmr (D₆-DMSO)δ4.9 (d,2H,J=46 Hz), 4.5 (s,H).

Example I

Tetrahydro-4H-pyran-4-yl 3-amino-2-butenoate

Colourless crystals mp 88°-90°.

Example J

1-Ethylpropyl 3-amino-2-butenoate

Pale yellow oil, bp 143°-8°/12 mm Hg.

Example K (S)-2,2,2-Trichloro-1-phenylethyl 3-oxobutanoate

Diketene (3.7 ml, 47 mmoles) was added slowly to a stirred mixture of (S)-alpha-(trichloromethyl) phenylmethanol (9.2 g, 41 mmoles) and triethylamine (0.05 ml) kept at 80°-90°. The mixture was maintained for 5 hours at 90°The cooled reaction mixture was purified using HPLC eluting with methylene chloride/petroleum ether 60°-80° to give the title compound (11 g) as an oil. Nmr (CDCl₃)δ6.39 (s,H), 3.61 (s,2H), 2.31 (s,3H).

The compound of Example L was obtained by the same method.

Example L 2,2,2-Trichloro-1-phenylethyl 3-oxobutanoate

Colourless solid, nmr (CDCl₃)δ6.39 (s,H), 3.61 (s,2H), 2.31 (s,3H).

Example M

Tetrahydro-4H-pyran-4-yl 3-oxobutanoate

A solution of tetrahydro-4H-pyran-4-ol (1.6 ml, 16.8 mmoles) and 5-acetyl-2,2-dimethyl-1,3-dioxane-4,6-dione (3.0 g, 16.1 mmoles) in dry benzene (50 ml) was heated under reflux for 4 hours. The solvent was removed in vacuo and the residue distilled at 146°-151°/14 mm Hg to afford the title product as a colourless oil, 2.84 g. Nmr (CDCl₃)δ5.1 (m,H), 3.5 (s,3H).

The esters of Examples N to R were prepared using appropriate starting materials and the method of Example M.

Example N

1-Ethylpropyl 3-oxobutanoate

Colourless oil, bp 128°-38° (bath temp)/14 mm Hg.

Example O

1-Methyl-1-phenylethyl 3-oxobutanoate

Colourless oil, bp 108°-110° (bath temp)/0.03 mm Hg.

Example P

1-Methylcyclopentyl 3-oxobutanoate

Colourless oil, bp 134°-145° (bath temp)/14 mm Hg.

Example Q 4-(1-Diphenylmethylazetidinyl) 3-oxobutanoate

Pale yellow oil. M+ 323

Example R

3-Oxetanyl 3-oxobutanoate

Pale yellow oil 165°-70° (bath temp)/12 mm Hg.

Example S

1-Chloro-4-fluoro-2-(trifluoromethyl)benzene

4-Chloro-3-(trifluoromethyl)benzenamine (19.5 g, 100 mmoles), water (40 ml) and c.hydrochloric acid (40 ml) were heated with stirring on a steam bath until a white solid formed. The mixture was cooled (ice-salt bath) and a solution of sodium nitrite (7 g, 101 mmoles) in water (15 ml) was added over 15 mins. After stirring for a further hour at 0°, tetrafluoroboric acid (30 g of 40% aqueous solution) was added dropwise over 15 minutes. After one hour the solid was filtered off, washed with water (10 ml), methanol (30 ml) and ether (30 ml) and then dried in vacuo. The dry compound was heated at 140°-180° until no more fumes were observed. The cooled residue was dissolved in ethyl acetate, washed with 5% aqueous sodium hydroxide, dried (Na₂SO₄) and the solvent was removed in vacuo. The residue was distilled in vacuo (12 mmHg, oven temperature 50°-55°) to give the sub-title compound as a colourless oil (7.5 g). M+ 200/198; nmr (CDCl₃)δ7.8-7.2 (m).

Example T

2-Chloro-5-fluoro-3-(trifluoromethyl)benzaldehyde and 3-Chloro-6-fluoro-2-(trifluoromethyl)benzaldehyde Butyl lithium (60.4 ml of 1.6M in hexane, 97 mmoles) was added with stirring over 1.5 hours under nitrogen to a solution of 1-chloro-4-fluoro- 2-(trifluoromethyl)-benzene (17.8 g, 91 mmoles) in dry tetrahydrofuran (150 ml) at −73°. After a further 1.5 hours at this temperature, N-methyl-N-phenylformamide (10.86 ml, 90 mmoles) in dry tetrahydrofuran (20 ml) was added over 0.5 hours. After 15 minutes the reaction mixture was poured onto 10% aqueous sulphuric acid. The ethereal layer was separated, washed with saturated sodium bicarbonate, dried (Na₂SO₄) and the solvent evaporated. The residue was purified by HPLC eluting with ethyl acetate/petroleum ether 60°-80° mixtures 2-Chloro-5-fluoro-3-(trifluoromethyl) benzaldehyde (0.5 g) was eluted first.

M+ 226/228; nmr (CDCl₃)δ10.5 (s,H).

Further elution afforded 3-chloro-6-fluoro-2-(trifluoromethyl)benzaldehyde (8.35g).

M+226/228; nmr (CDCl₃) 10.5 (q,H).

Example U

2-Chloro-3-(trifluoromethyl) benzaldehyde

Butyl lithium (36.4 ml of 1.6M in hexane) was added to a stirred solution at −65° of 1-chloro-2-(trifluoromethyl)-benzene (10 g) in dry tetrahydrofuran (100 ml) over 20 mins. After stirring for 1.5 hours at −65°, a solution of N-methyl-N-phenylformamide (6.85 ml) in tetrahydrofuran (30 ml) was added over 1 hour. The reaction mixture was left at this temperature for 1.5 hours and then allowed to reach room temperature. It was then poured onto 10% sulphuric acid, extracted with ether and the organic extract was washed with brine, dried (Na₂SO₄) and the solvent removed in vacuo. The residue was distilled (20 mmHg, oven temperature 100°–125°); the distillate was cooled, filtered and the solid washed with petroleum ether (60°–80°) to give the desired aldehyde (3.5 g) as a colourless solid. M+ 210/208, nmr (CDCl$_3$)$\delta$10.75 (s,H).

Example V

2,3-Dichloro-6-fluorobenzaldehyde

Butyl lithium (48 ml of 1.6M in hexane, 52.3 mmoles) was added with stirring over 1.5 hours under nitrogen to a solution of 1,2-dichloro-4-fluorobenzene (7.85 g, 47.6 mmoles) in dry tetrahydrofuran (120 ml) at −68°. The solution was stirred at −68° for 2 hours and then N-methyl-N-phenylformamide (6.48 ml) in dry tetrahydrofuran (15 ml) was added over 1.5 hours. After a further 1.5 hours at −68°, the reaction mixture was poured into 10% aqueous sulphuric acid and ether. The ethereal layer was separated, washed with brine, dried (Na$_2$SO$_4$) and evaporated to give the desired aldehyde (8 g). M+ 196/194/192, nmr (CDCl$_3$)$\delta$10.5 (s,H).

Example W

Diethyl 1,2,3,4-tetrahydro-2-hydroxy-6-methyl-4-(3-nitrophenyl)-2-(trifluoromethyl)-3,5-pyridinedicarboxylate (starting material for Example 68)

3-Nitrobenzaldehyde (3.0 g, 20 mmoles), ethyl 3-amino-2-butenoate (2.6 g, 20 mmoles) and ethyl 4,4,4-trifluoro-3-oxobutanoate (2.92 ml, 20 mmoles) were heated at reflux in ethanol (25 ml) for 6 hours. The solvent was removed in vacuo and the residue crystallised by the addition of ether/petroleum ether (60°–80°). The resulting solid was recrystallised from ether/petroleum ether (60°–80°) to give the title compound as colourless crystals (1.9 g) mp 120°–1°.

The starting materials for Examples 70 and 71 were also made using appropriate starting materials and the process of Example W.

The starting materials for Examples 65 to 69 inclusive were made using appropriate starting materials and the process of Example 79.

The starting material for Example 72 was made using appropriate starting materials and the method of Examples 50 to 52.

Example X

| | % w/w | Range % w/w |
|---|---|---|
| Compound of formula I | 5 | 1–20 |
| Microcrystalline cellulose | 50 | 10–80 |
| Spray dried lactose | 37.75 | 10–80 |
| Magnesium stearate | 1 | 0.25–2 |
| Colloidal silicon dioxide | 0.25 | 0.1–1 |
| Cross linked sodium carboxy methyl cellulose | 3 | 1–5 |
| Hydroxypropylmethylcellulose (coating) | 3 | 1–5 |

This formulation is made up as a direct compression table, or without compression or coating, may be filled into a gelatine capsule.

Example Y

| | % w/w | Range % w/w |
|---|---|---|
| Compound of formula I | 5 | 1–20 |
| Microcrystalline cellulose | 50 | 10–80 |
| Lactose | 35.75 | 10–80 |
| Polyvinylpyrrolidone | 2 | 1–5 |
| Magnesium stearate | 1 | 0.25–2 |
| Colloidal silicon dioxide | 0.25 | 0.1–1 |
| Cross linked sodium carboxy methyl cellulose | 3 | 1–5 |
| Hydroxypropyl methyl cellulose (coating) | 3 | 1–5 |

This formulation is made up as a granulate and then compressed into a tablet. Alternatively the granules may be filled into a gelatine capsule.

We claim:

1. A compound of formula I,

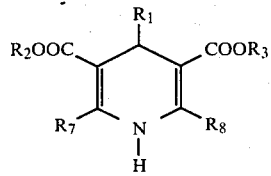

in which

R$_1$ represents benzolfurazanyl, pyridyl or phenyl, the pyridyl or phenyl being substituted by one or more of the groups halogen, nitro, —CN, —OR$_9$, —S(O)$_p$R$_9$, or alkyl C$_1$ to C$_6$ optionally substituted by halogen, p is 0, 1 or 2, R$_2$ and R$_3$, which may be the same or different, each represent hydrogen; alkyl C$_1$ to C$_6$ optionally substituted by one or more of the groups halogen, cyano, —XR$_4$, —NR$_5$R$_6$ or phenyl; cycloalkyl C$_3$ to C$_8$ optionally substituted by alkyl C$_1$ to C$_6$; oxetanyl, azetidinyl, piperidinyl or tetrahydropyranyl, each of which is optionally substituted by alkyl C$_1$ to C$_6$, the alkyl in turn optionally being substituted by one or more phenyl groups, R$_5$ and R$_6$, which may be the same or different, each represent alkyl C$_1$ to C$_6$ optionally substituted by phenyl, one of R$_7$ and R$_8$ represents alkyl C$_1$ to C$_6$ and the other represents alkyl C$_1$ to C$_6$ substituted by only one fluorine atom;

X is O or S,

R$_4$ is alkyl C$_1$ to C$_6$ or phenyl,

R$_9$ is alkyl C$_1$ to C$_6$, and pharmaceutically acceptable acid addition salts of those compounds containing a basic nitrogen atom.

2. A compound according to claim 1, wherein R$_1$ is nitrophenyl; (trifluoromethyl)phenyl; mono- or poly-fluorophenyl; mono- or poly-chlorophenyl; chloro- and/or fluoro-(trifluoromethyl)phenyl; (alkylthio)pyridyl; alkyl- and/or chloro- and/or alkoxy-nitrophenyl; mixed chloro- and fluoro-phenyl; mono- or poly- alkoxy-phenyl; alkylphenyl; (alkylthio)phenyl; (alkylsulphonyl)phenyl, or 4-benzofurazanyl, R$_2$ and R$_3$ are selected from alkyl C$_1$ to C$_4$; 2-alkoxy C$_1$ to C$_3$-ethyl; 2-phenoxy- ethyl; cycloalkyl C$_4$ to C$_6$ optionally substituted by methyl; an oxetanyl, azetidinyl, Piperidinyl or tetrahydropyranyl ring optionally substituted by phenylmethyl or diphenylmethyl; alkyl C$_1$ to C$_4$-(phenylmethyl)aminoethyl; cyano- or alkyl $C_1$ to $C_4$-thio- alkyl $C_1$ to $C_4$; phenyl alkyl $C_1$ to $C_4$ or —CH($C_6H_5$)CCl$_3$, $R_7$ is methyl, and $R_8$ is fluoro- alkyl $C_1$ or $C_2$.

3. A compound according to claim 1, wherein $R_1$ is phenyl carrying a 2-nitro or a 2—CF$_3$ group or at least two substituents selected from chloro, fluoro, alkyl $C_1$ to $C_6$, —CF$_3$ and nitro; $R_2$ is alkyl C1 to 6, or is oxetan -3-yl, $R_3$ is alkyl $C_1$ to $C_6$, $R_7$ is alkyl $C_1$ to $C_6$, and $R_8$ is fluoromethyl.

4. A compound according to claim 1, wherein $R_1$ is phenyl carrying at least two substituents selected from chloro, fluoro, —CF$_3$, methyl and nitro, $R_3$ and $R_7$ are both methyl, $R_8$ is —CH$_2$F, and $R_2$ is isopropyl or cyclopentyl.

5. A compound according to claim 1, wherein $R_1$ represents benzofurazanyl, pyridyl or phenyl, the pyridyl or phenyl being substituted by one or more of the groups halogen, nitro, trihalomethyl or —SR$_9$; $R_2$ and $R_3$ each represent alkyl $C_1$ to $C_6$, —(CH$_2$)$_n$ X R$_4$, —(CH$_2$)$_n$CN, —CH($C_6H_5$)CCl$_3$ or —(CH$_2$)$_n$—NR$_5$R$_6$ wherein n is 2, 3 or 4.

6. A compound according to claim 1 which is 3-Methyl 5-(1-methylethyl) 4-(3-chloro-6-fluoro-2-(trifluoromethyl)phenyl)-2-(fluoromethyl)-1,4-dihydro-6-methyl-3,5-pyridinedicarboxylate.

7. A compound according to claim 1 which is 3-methyl 4-(2,3-dichlorophenyl)-2-(fluoromethyl)-1,4-dihydro-6-methyl-3,5-pyridinedicarboxylate.

8. A compound according to claim 1 and selected from

3-Methyl 5-(1-methylethyl) 4-(2,3-dichlorophenyl)-2-(fluoromethyl)-1,4-dihydro-6-methyl-3,5-pyridinedicarboxylate, 3-Methyl 5-(1-methylethyl) 2-(fluoromethyl)-1,4-dihydro-6-methyl-4-(2-methyl-3-nitrophenyl)-3,5-pyridinedicarboxylate, 5-Cyclopentyl 3-methyl 4-(2,3-dichlorophenyl)-2-(fluoromethyl)-1,4-dihydro-6-methyl-3,5-pyridinedicarboxylate, 3-Methyl 5-(1-methylethyl) 4-(2-chloro-3-nitrophenyl)-2-(fluoromethyl)-1,4-dihydro-6-methyl-3,5-pyridinedicarboxylate, 3-Methyl 5-(1-methylethyl) 2-(fluoromethyl)-4-(2-fluoro-6-(trifluoromethyl)phenyl)-1,4-dihydro-6-methyl-3,5-pyridinedicarboxylate, 3-Methyl 5-(1-methylethyl) 4-(2,3-dichloro-6-fluorophenyl)-2-(fluoromethyl)-1,4-dihydro-6-methyl-3,5-pyridinedicarboxylate, 5-Ethyl 3-methyl 2-(fluoromethyl)-1,4-dihydro-6-methyl-4-(3-nitrophenyl)-3,5-pyridinedicarboxylate, 3-Methyl 5-(1-methylethyl) 2-(fluoromethyl)-1,4-dihydro-6-methyl-4-(3-nitrophenyl)-3,5-pyridinedicarboxylate, 3-Methyl 5-(2-methylpropyl) 2-(fluoromethyl)-1,4-dihydro-6-methyl-4-(3-nitrophenyl)-3,5-pyridinedicarboxylate, 3-Ethyl 5-methyl 2-(fluoromethyl)-1,4-dihydro-6-methyl-4-(3-nitrophenyl)-3,5-pyridinedicarboxylate, Diethyl 2-(fluoromethyl)-1,4-dihydro-6-methyl-4-(2-(trifluoromethyl)phenyl)-3,5-pyridinedicarboxylate, Diethyl 4-(4 benzofurazanyl)-2-(fluoromethyl)-1,4-dihydro-6-methyl-3,5-pyridinedicarboxylate, Dimethyl 2-(fluoromethyl)-1,4-dihydro-6-methyl-4(2,3,4,5,6-pentafluorophenyl)-3,5-pyridinedicarboxylate, 5-Methyl 3-(1-methylethyl) 2-(fluoromethyl)-1,4-dihydro-6-methyl-4-(3-nitrophenyl)-3,5-pyridinedicarboxylate, 5-Ethyl 3-methyl 4-(2,3-dichlorophenyl)-2-(fluoromethyl)-1,4-dihydro-6-methyl-3,5-pyridinedicarboxylate, Diethyl 2-(fluoromethyl)-1,4-dihydro-6-methyl-4(2-(methylthio)-3-pyridyl)-3,5-pyridinedicarboxylate, 3-Methyl 5-(2-(methyl(phenylmethyl)amino)ethyl) 2-(fluoromethyl)-1,4-dihydro-6-methyl-4-(3-nitrophenyl)-3,5-pyridinedicarboxylate oxalate, 5-(2-Methoxyethyl) 3-(1-methylethyl) 4-(2,3-dichlorophenyl)-2-(fluoromethyl)-1,4-dihydro-6-methyl-3,5-pyridinedicarboxylate, 5-(2-Cyanoethyl) 3-(1-methylethyl) 2-(fluoromethyl)-1,4-dihydro-6-methyl-4-(3-nitrophenyl)-3,5-pyridinedicarboxylate, 3-(1-Methylethyl) 5-(2-methylthio)ethyl) 2-(fluoromethyl)-1,4-dihydro-6-methyl-4-(3-nitrophenyl)-3,5-pyridinedicarboxylate, 3-Methyl 5-(1-methylethyl) 4-(2-chloro-5-nitrophenyl)-2-(fluoromethyl)-1,4-dihydro-6-methyl-3,5-pyridinedicarboxylate, 3-Ethyl 5-methyl 4-(2,3-dichlorophenyl)-2-(fluoromethyl)-1,4-dihydro-6-methyl-3,5-pyridinedicarboxylate, 3-Methyl 5-(1-methylethyl) 2-(fluoromethyl)-1,4-dihydro-6-methyl-4-(2-methyl-5-nitrophenyl)-3,5-pyridinedicarboxylate, 3-(2-Methoxyethyl) 5-(1-methylethyl) 2-(fluoromethyl)-1,4-dihydro-6-methyl-4-(3-nitrophenyl)-3,5-pyridinedicarboxylate, 5-(2-Methoxyethyl) 3-(1-methylethyl) 2-(fluoromethyl)-1,4-dihydro-6-methyl-4-(3-nitrophenyl)-3,5-pyridinedicarboxylate, 3-Methyl 5-(1-methylethyl) 4-(2-chloro-3-(trifluoromethyl)phenyl)-2-(fluoromethyl)-1,4-dihydro-6-methyl3,5-pyridinedicarboxylate, 5-(1-Methylethyl) 3-(tetrahydro-4H-pyran-4-yl) 2-(fluoromethyl)-1,4-dihydro-6-methyl-4-(3-nitrophenyl)-3,5-pyridinedicarboxylate;

5-(1-Methylethyl) 3-(2-phenoxyethyl) 2-(fluoromethyl)-1,4-dihydro-6-methyl-4-(3-nitrophenyl)-3,5-pyridinedicarboxylate, 5-Methyl 3-(tetrahydro-4H-pyran-4-yl) 2-(fluoromethyl)-1,4-dihydro-6-methyl-4-(3-nitrophenyl)-3,5-pyridinedicarboxylate, 5-Cyclohexyl 3-methyl 4-(2,3-dichlorophenyl)-2-(fluoromethyl)-1,4-dihydro-6-methyl-3,5-pyridinedicarboxylate, 5-Cyclopentyl 3-methyl 2-(fluoromethyl)-1,4-dihydro-6-methyl-4-(2-methyl-3-nitrophenyl)-3,5-pyridinedicarboxylate, 3-Methyl 5-(1-methylethyl) 4-(2,3-dimethoxyphenyl)-2-(fluoromethyl)-1,4-dihydro-6-methyl-3,5-pyridinedicarboxylate, 3-Methyl 5-(tetrahydro-4H-pyran-4-yl) 4-(2,3-dichlorophenyl)-2-(fluoromethyl)-1,4-dihydro-6-methyl-3,5-pyridinedicarboxylate, 5-Cyclopentyl 3-methyl 2-(fluoromethyl)-1,4-dihydro-6-methyl-4-(2-(trifluoromethyl)phenyl)-3,5-pyridinedicarboxylate, 5-Cyclopentyl 3-methyl 4-(3-chloro-6-fluoro-2-(trifluoromethyl)phenyl)-2-(fluoromethyl)-1,4-dihydro-6-methyl-3,5-pyridinedicarboxylate, 5-(1-Ethylpropyl) 3-methyl 4-(2,3-dichlorophenyl)-2-(fluoromethyl)-1,4-dihydro-6-methyl-3,5-pyridinedicarboxylate, 3-Methyl 5-(1-methylethyl) 2-(fluoromethyl)-1,4-dihydro-4-(2-methoxy-3-nitrophenyl)-6-methyl-3,5-pyridinedicarboxylate, 3-Methyl 5-(1-methylethyl) 2-(fluoromethyl)-1,4-dihydro-6-methyl-4-(2-trifluoromethyl)phenyl)-3,5-pyridinedicarboxylate, 3-Methyl 5-(1-methylethyl) 2-(fluoromethyl)-1,4-dihydro-6-methyl-4-(2-nitrophenyl)-3,5-pyridinedicarboxylate, 3-Methyl 5-(1-methylethyl) 2-(fluoromethyl)-4-(2-fluorophenyl)-1,4-dihydro-6-methyl-3,5-pyridinedicarboxylate, 3-Methyl 5-(1-methylethyl) 2-(fluoromethyl)-1,4-dihydro-6-methyl-4-(2-(methylphenyl)-3,5-pyridinedicarboxylate, 3-Methyl 5-(1-methylethyl) 4-(2-chlorophenyl)-2-(fluoromethyl)-1,4-dihydro-6-methyl-3,5-pyridinedicarboxylate, 3-Methyl 5-(1-methylethyl) 2-(fluoromethyl)-1,4-dihydro-6-methyl-4-(2-(methylthio)phenyl)-3,5-pyridinedicarboxylate, 3-Methyl 5-(1-methylethyl) 2-(fluoromethyl)-1,4-dihydro-6-methyl-4-(2-(methylsulphonyl)phenyl)-3,5-pyridinedicarboxylate, 3-Methyl 5-(1-methylethyl) 4-(3-chloro-2-methylphenyl)-2-(fluoromethyl)-1,4-dihydro-6-methyl-3,5-pyridinedicarboxylate, 3-Methyl 5-(1-methylethyl) 4-(2,3-dimethylphenyl)-2-(fluoromethyl)-1,4-dihydro-6-methyl-3,5-pyridinedicarboxylate, 3-Methyl 5-(1-methylethyl) 4-(3-cyanophenyl)-2-(fluoromethyl)-1,4-dihydro-6-methyl-3,5-pyridinedicarboxylate, 3-Methyl 5-(1-methylethyl) 4-(3-chlorophenyl)-2-(fluoromethyl)-1,4-dihydro-6-methyl-3,5-pyridinedicarboxylate, 5-Cyclobutyl 3-methyl 4-(2,3-dichlorophenyl)-2-(fluoromethyl)-1,4-dihydro-6-methyl-3,5-pyridinedicarboxylate, 3-Methyl 5-(3-oxetanyl) 4-(2,3-dichlorophenyl)-2-(fluoromethyl)-1,4-dihydro-6-methyl-3,5-pyridinedicarboxylate, 3-Methyl 5-((S)-2,2,2-trichloro-1-phenylethyl) 4-2,3-dichlorophenyl)-2-(fluoromethyl)-1,4-dihydro-6-methyl-3,5-pyridinedicarboxylate, 3-Methyl 5-(2,2,2-trichloro-1-phenylethyl) 4-(2,3-dichlorophenyl2-(Fluoromethyl)-1,4-dihydro-6methyl-3,5-pyridinedicarboxylate.

5-(1-Diphenylmethyl)-3-azetidinyl) 3-methyl 4-(2,3-dichlorophenyl)-2-(fluoromethyl)-1,4-dihydro-6-methyl-3,5-pyridinedicarboxylate, 3-Methyl 5-(1-(phenylmethyl)-4-piperidinyl) 4-(2,3-dichlorophenyl)-2-(fluoromethyl)-1,4-dihydro-6-methyl-3,5-pyridinedicarboxylate, 5-(1,1-Dimethylethyl) 3-methyl 4-(2,3-dichlorophenyl)-2-(fluoromethyl)-1,4-dihydro-6-methyl-3,5-pyridinedicarboxylate, 3-Methyl 5-(1-methyl-1-phenylethyl) 4-(2,3-dichlorophenyl)-2-(fluoromethyl)-1,4-dihydro-6-methyl-3,5-pyridinedicarboxylate, 3-Methyl 5-(1-methylcyclopentyl) 4-(2,3-dichlorophenyl)-2-(fluoromethyl)-1,4-dihydro-6-methyl-3,5-pyridinedicarboxylate, 3-Methyl 5-(2,2,2-trichloro-1-phenylethyl) 2-(fluoromethyl)-1,4-dihydro-6-methyl-4-(3-nitrophenyl)-3,5-pyridinedicarboxylate, Diethyl 2-(fluoromethyl)-1,4-dihydro-6-methyl-4-(3-nitrophenyl)-3,5-pyridinedicarboxylate, Di-(2-propoxyethyl) 2-(fluoromethyl)-1,4-dihydro-6-methyl-4-(3-nitrophenyl)-3,5-pyridinedicarboxylate, Diethyl 2-(fluoromethyl)-1,4-dihydro-6-methyl-4-(3-nitrophenyl)-3,5-pyridinedicarboxylate, (+) 3-Methyl 5-(1-methylethyl) 4-(2,3-dichlorophenyl)-2-(fluoromethyl)-1,4-dihydro-6-methyl-3,5-pyridinedicarboxylate, (−) 3-Methyl 5-(1-methylethyl) 4-(2,3-dichlorophenyl)-2-(fluoromethyl)-1,4-dihydro-6-methyl-3,5-pyridinedicarboxylate, (+) 5-cyclopentyl 3-methyl 4-(2,3-dichlorophenyl)-2-(fluoromethyl)-1,4-dihydro-6-methyl-3,5-pyridinedicarboxylate, (−) 5-Cyclopentyl 3-methyl 4-(2,3-dichlorophenyl)-2-(fluoromethyl)-1,4-dihydro-6-methyl-3,5-pyridinedicarboxylate, and 3-Methyl 4-(2,3-dichlorophenyl)-2-fluoromethyl)-1,4-dihydro-6-methyl-3,5-pyridinedicarboxylate.

9. A method of treatment of renovascular, malignant or essential hypertension, pulmonary hypertension, vasospastic angina, chronic stable angina or congestive heart failure, which comprises administering an effective amount of a compound according to claim 1 to a patient suffering from such a condition.

10. A pharmaceutical composition for the treatment of renovascular, malignant or essential hypertension, pulmonary hypertension, vasospastic angina, chronic stable angina or congestive heart failure, said composition containing an amount of a compound according to claim 1 effective for said treatment, in admixture with a pharmaceutically acceptable adjuvant, diluent, or carrier.

* * * * *